US009675273B2

(12) United States Patent
Gluncic

(10) Patent No.: US 9,675,273 B2
(45) Date of Patent: Jun. 13, 2017

(54) SYSTEM AND METHODS FOR IDENTIFICATION OF IMPLANTED MEDICAL DEVICES AND/OR DETECTION OF RETAINED SURGICAL FOREIGN OBJECTS FROM MEDICAL IMAGES

(71) Applicant: RUSH UNIVERSITY MEDICAL CENTER, Chicago, IL (US)

(72) Inventor: Vicko Gluncic, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 15/131,000

(22) Filed: Apr. 17, 2016

(65) Prior Publication Data

US 2016/0228034 A1    Aug. 11, 2016

Related U.S. Application Data

(63) Continuation of application No. 14/361,386, filed as application No. PCT/US2012/067070 on Nov. 29, 2012, now Pat. No. 9,317,920.

(Continued)

(51) Int. Cl.
*G06T 7/00* (2017.01)
*A61B 6/12* (2006.01)
(Continued)

(52) U.S. Cl.
CPC .............. *A61B 5/066* (2013.01); *A61B 5/055* (2013.01); *A61B 5/4851* (2013.01); *A61B 6/12* (2013.01);
(Continued)

(58) Field of Classification Search
CPC ..... G06T 7/0012; G06T 7/0014; G06T 7/0044; G06T 2207/10072; G06T 2207/10116;
(Continued)

(56) References Cited

U.S. PATENT DOCUMENTS 6,418,335 B2    7/2002  Avrin et al. ................... 600/409
7,180,014 B2    2/2007  Farber et al. .............. 177/25.19
(Continued)

FOREIGN PATENT DOCUMENTS

GB        2459043 A        10/2009   ............... G06K 9/00
WO     WO 2011/094639 A2   8/2011    ............. G06Q 50/00
WO     WO 2011/103590 A2   8/2011    ............. G06Q 50/00

OTHER PUBLICATIONS

Search Report and Written Opinion issued in Int'l App. No. PCT/US2012/067070 (2013).

(Continued)

*Primary Examiner* — Andrew W Johns
(74) *Attorney, Agent, or Firm* — Alice O. Martin; Barnes & Thornburg LLP

(57) ABSTRACT

The present invention involves a computer-based system and method for detecting and identifying implantable medical devices ("IMDs") and/or retained foreign objects ("RFSOs") from diagnostic medical images. In some embodiments, the system provides further identification—information on the particular IMD or RSFO that has been recognized. For example, the system may be configures to provide information feedback regarding the IMD, such as detailed manual information, safety alerts, recall, access to its structural integrity, and/or suggested courses of action in a specific clinical setting/troubleshooting. Embodiments are contemplated in which the system is configured to report possible 3D locations of RSFOs in the surgical field/images.

9 Claims, 14 Drawing Sheets

Related U.S. Application Data

(60) Provisional application No. 61/564,949, filed on Nov. 30, 2011, provisional application No. 61/570,117, filed on Dec. 13, 2011, provisional application No. 61/659,780, filed on Jun. 14, 2012.

(51) Int. Cl.

| | | |
|---|---|---|
| *A61B 5/06* | (2006.01) | |
| *G06K 9/00* | (2006.01) | |
| *G06K 9/46* | (2006.01) | |
| *G06K 9/62* | (2006.01) | |
| *A61B 6/00* | (2006.01) | |
| *A61B 8/08* | (2006.01) | |
| *A61B 5/055* | (2006.01) | |
| *A61B 5/00* | (2006.01) | |
| *G06T 7/73* | (2017.01) | |
| *A61B 34/20* | (2016.01) | |
| *A61B 90/00* | (2016.01) | |

(52) U.S. Cl.
CPC .......... *A61B 6/5211* (2013.01); *A61B 8/0841* (2013.01); *A61B 8/5215* (2013.01); *G06K 9/00* (2013.01); *G06K 9/00214* (2013.01); *G06K 9/4604* (2013.01); *G06K 9/4671* (2013.01); *G06K 9/6211* (2013.01); *G06T 7/0012* (2013.01); *G06T 7/0014* (2013.01); *G06T 7/74* (2017.01); *A61B 6/563* (2013.01); *A61B 2034/2057* (2016.02); *A61B 2090/378* (2016.02); *A61B 2090/3762* (2016.02); *A61B 2576/00* (2013.01); *G06T 2207/10072* (2013.01); *G06T 2207/10116* (2013.01); *G06T 2207/10132* (2013.01); *G06T 2207/20068* (2013.01); *G06T 2207/30052* (2013.01)

(58) Field of Classification Search
CPC . G06T 2207/10132; G06T 2207/30052; G06T 7/74; A61B 6/12; A61B 6/5211; A61B 8/0833; A61B 8/0841; A61B 8/5215
See application file for complete search history.

(56) References Cited

U.S. PATENT DOCUMENTS

| | | | |
|---|---|---|---|
| 7,932,825 B2 | 4/2011 | Berger | 340/572.1 |
| 9,317,920 B2 * | 4/2016 | Gluncic | A61B 6/12 |
| | | | 382/128 |
| 2007/0238999 A1 | 10/2007 | Specht | 600/437 |
| 2009/0257655 A1 | 10/2009 | Melikian | 382/190 |
| 2010/0080426 A1 | 4/2010 | Schmitt et al. | 382/128 |
| 2010/0121190 A1 | 5/2010 | Pagoulatos et al. | 600/437 |
| 2012/0213444 A1 | 8/2012 | Melikian | 382/204 |
| 2013/0053680 A1 | 2/2013 | Frey | 600/411 |

OTHER PUBLICATIONS

Search Report issued in EP App. No. 12852687.8 (2015).
MacFarlane et al., "A Searchable medical implant database for safety in the medical resonance environment," *Radiogaphy*, 14(4): 362-265 (2008).
Office Action issued in EP App. No. 12852687.8 (Aug. 5, 2016).

* cited by examiner

SYSTEM AND METHODS FOR IDENTIFICATION OF IMPLANTED MEDICAL DEVICES AND/OR DETECTION OF RETAINED SURGICAL FOREIGN OBJECTS FROM MEDICAL IMAGES

CROSS-REFERENCE TO RELATED APPLICATIONS

This application claims the benefit of priority from pending U.S. patent application Ser. No. 14/361,386, May 29, 2014, now U.S. Pat. No. 9,317,920, which is a national stage of International Patent Application Serial No. PCT/US2012/067070, filed on Nov. 29, 2012, which claims priority to U.S. Provisional Application Ser. No. 61/564,949, filed Nov. 30, 2011, U.S. Provisional Application Ser. No. 61/570,117, filed Dec. 13, 2011, and U.S. Provisional Application Ser. No. 61/659,780, filed Jun. 14, 2012. Each of these applications is incorporated herein by reference in its entirety.

BACKGROUND

Medical pattern recognition software is known, and has become important in many areas of medical analysis.

Approximately 25 million patients in the United States have or have had an implanted or implantable medical device ("IMD"). Driven by a rapidly increasing aged population and supported by new technologies, the demand for IMDs and their further proliferation can only be expected to increase.

An IMD is a medical device that is partly or totally surgically inserted into the human body or a natural orifice and is expected to remain implanted for an extended period or may be permanent. IMDs can further be classified as either active, those that use electricity, or passive, those that do not use electricity. In the US, medical devices are regulated by the FDA and classified into three classes, on basis of risk and the level of regulatory control that is necessary to assure the safety and effectiveness: class I, class II, and class III. Class III devices include devices that generally affect the functioning of vital organs and/or life support systems with very high health risk if the device were to malfunction.

Identification of an IMD during patient admission, and especially in emergencies, is crucial for the safe and efficient management of that patient. Concerns with the accurate and timely identification of IMDs are an emerging safety issue. Of particular concern is the commonly encountered situation where medical records are not available and/or the patient is unable to provide the appropriate information/documentation regarding the IMD he has. Most commonly IMDs are initially reported by patients or noted on admission and/or emergency x-rays ("XRs"), magnetic resonance images ("MRI"), ultrasound or computerized tomography ("CT") images, necessitating, often ineffective, attempts to gather more information regarding the device in question. This usually involves contacting the patient's family, primary care providers or health care institutions previously visited by the patient. Even when such attempts are successful, available information about the patient's device is often incomplete, unreliable and delayed. On the other hand, the large variety, rapidly increasing number approved by FDA, and difficult projections/orientations of IMDs in medical images (XR, CT, or MRI) make their identification very difficult for radiology specialists. Possible consequences include: delayed appropriate diagnostic imaging and care, medical complications arising from device incompatibility with imaging or therapeutic modalities, and suboptimal care due to inappropriate avoidance of treatment and diagnostic procedures that are erroneously considered contraindicated.

Software applications facilitate initial assessment/identification, expedite the management, and improve the healthcare and safety of patients with IMDs, including those with symptoms of IMD malfunction. They also facilitate implementation of recent FDA requirements for post-market device surveillance.

Physicians are increasingly encountering patients with IMDs. Identification of an IMD, during an emergent admission in particular, is critical for safe and efficient patient management. In 2007, FDA issued a report indicating an increase in adverse events linked to medical devices, including 2,830 deaths, 116,086 injuries, and 96,485 device malfunctions. Class III active IMDs were cited in a relatively high number of fatality reports within the FDA report.

Ultra-low-power radio-frequency (RF) technology has greatly facilitated the development of IMDs. The ability to wirelessly transmit the patient's and IMD's data enables a clinician to obtain useful diagnostic information and reprogram therapeutic settings. Furthermore, radio-frequency identification (RFID) technology uses radio waves to transfer data from an electronic tag to identify and track the tagged device. However, the rapidly increasing number of IMDs and their manufacturers, absence of the standardized tools/methods capable of RF sensing, identifying, and reprogramming IMDs, radio interference problems, ethical/security issues, and the fact that many IMDs do not have RF capabilities make this technology less convenient for rapid identification. This disadvantage is particularly obvious in medical emergencies and emergency room settings.

Medical errors involving IMDs, especially those arising from their incompatibility with treatment or diagnostic procedures, are an emerging patient safety issue. Procedures incompatible with patient's devices have been performed, leading to device malfunction and other complications. Examples of such complications include: patients undergoing Magnetic Resonance Imaging (MRI) in the presence of implanted ferromagnetic devices possibly causing migration, interference with the function of implanted devices because of strong magnetic fields (MR) and disrupting electrical forces (certain types of CT or surgical electrocautery). This includes setting changes of active (none turned off) cardiac pacemakers and defibrillators and/or defibrillation shocks during surgical procedures caused by electrocautery scalpels. In another example, percutaneous catheters and ports have been damaged by exceeding their pressure ratings during therapeutic infusions, necessitating subsequent surgical interventions/exchange or repair. Furthermore, several IMDs are compatible with MRI and CT imaging but/and/or requires reprogramming after the completion of the MRI which has been frequently missed. These effects on the IMD are not always evident or immediately observed (such as unintended re-programming, e.g., ventriculo-peritoneal shunts' valves) and can not only lead to delays but also to serious and possibly disastrous complications. Conversely, there are patients that do not receive optimal treatment and diagnostic procedures, even though their devices are compatible with such treatments. For example, several pacemakers currently on the market are compatible with MRI. In these cases, disclosure software identifies these specific models as being compatible with MRI, providing the treating physicians an option to have their patient undergo a medically-indicated MRI scan safely.

Retained surgical foreign objects (RSFOs) in patients, including needles and surgical instruments and/or materials, continues to be a significant problem with an incidence of between 0.3 and 1.0 per 1,000 surgeries. This has resulted in a significant increase in patient care costs and consecutive legal expenses.

Intra-operative or early post-operative identification of RSFOs is critical for safe and efficient management of surgical patients. Current recommendations for prevention of RSFOs in the operating room ("OR") include methodical wound exploration before closing, usage of standardized practices for surgical items accounting, usage of items with radio-opaque markers within the operative site, and mandatory operative field X-rays before wound closure when a item count discrepancy occurs. In addition, radiographic screening is recommended at the end of an emergent surgical procedure, unexpected change in the procedure, and for patients with a high body mass index. Some institutions also conduct routine postoperative screening radiographs for the prevention of RSFOs. Therefore, portable X-ray radiological protocols have become crucial for timely RSFO detection. However, they have relatively low efficacy and require significant time for completion and for evaluation. The underlying problems of their use are the relatively low sensitivity and specificity of the human eye in the identification of relatively small objects in a large X-ray field and the fact that radiologists and surgeons do not routinely undertake formal training in the recognition of RSFOs.

Technological aids to assist the OR team in the detection and prevention of retained sponges, gauze towels, and laparotomy pads include radio-frequency detectable sponge systems and bar-coded sponge systems. These aids are intended to augment the standardized manual count practices, and to not replace them.

Operative field X-ray is mandatory when there is a counting discrepancy of surgical instruments or materials at the end of the procedure. According to the 2006 Patient Care Memorandum of the Department of Veterans Affairs (Boston Healthcare System, VA, USA), surgical instruments and/or materials must be counted, except for procedures that are routinely concluded with a radiograph (for example, an orthopedic case to assure proper alignment of a bone or implant). In these cases, a radiograph is mandatory if an instrument count is not performed, and the evaluation of the radiograph must be performed before the patient is transferred from the OR to determine whether any instruments have been retained. When a radiograph is requested to locate a missing item, the type of foreign object that is missing, OR number, and telephone number must be specified in the request to the radiologist. Radiographic screening is also recommended/mandatory at the end of emergent surgical procedures, unexpected changes in procedures, or in patients with high BMI (e.g. >=20). Some institutions use postoperative screening radiographs routinely. In all of these cases, the completion of the surgical case may be delayed until radiologic evaluation is received. Assuming the patient is stable, current recommendations are that in the event of an incorrect count, a X-ray of the operative field should be made available to a radiologist within 20 minutes and their evaluation/confirmation of the results of the x-ray should be provided back to the OR within another 20 minutes. This process frequently takes significantly more time than 40 minutes.

Portable X-ray is also a method of choice for determination of the relative position/location of a RSFO. This is particularly important if the specific tissue layer or surgical incision/wound is already closed and additional instruments are present in the X-ray image.

While stainless steel instruments are likely to be detected successfully on radiograph screening, radiographs are less sensitive in detecting sponges and needles. Sponges may be difficult to detect because they may become twisted or folded, distorting visualization of the marker. Needles may also be difficult to visualize due to their size. The value of intraoperative and/or post-operative X-ray images for RSFO identification has been controversial and very few studies have been undertaken to evaluate their effectiveness. A recent study evaluating portable X-rays for identification of retained suture needles in ophthalmologic surgical cases showed that the overall sensitivity and specificity of the physicians' review of radiographs with suspected retained needles was 54% and 77%, respectively. This is particularly worrisome considering that in this particular case the size of the surgical field was small, the area of interest well-defined, while the participants in the study have known that they were looking for the needles which should have greatly facilitated RSFOs/needle detection. In the most studies when radiographs were falsely negative for RSFO detection; poor-quality radiographs, multiple foreign objects in the field, and failure to communicate the purpose of the radiograph to the interpreting radiologist were cited as contributing factors. Although it is mandatory that such intra-operative radiographs be reviewed by a radiologist(s) and/or surgeon(s), it is not routine for those individual to have undertaken specific/formal training in the radiographic identification/recognition of these objects. Furthermore, the general consensus throughout the literature is that the most effective means of evaluating the presence of a RSFO is through the use of CT scanning which—in most of the cases—is not possible in the OR.

SUMMARY

A diagnostic image analysis system is described with a method which allows for the identification of implanted medical devices ("IMDs") and provision of context relevant information to the physician relating to the patient and IMD identification and management.

Software tools based on pattern/object recognition and computer vision algorithms (but not limited only to these) are disclosed that are capable of rapid recognition of IMDs on x-rays ("XRs"), computer tomography ("CT"), ultra-sound ("US"), and magnetic resonance imaging ("MRI") images. This pattern recognition technology is integrated into the picture archiving and communication system ("PACS") environment used in health care environments to display radiological images and information. IMD recognition software recognizes the specific IMD, connects to an external data base which contains comprehensive and most current information on the specific IMD, and provides the clinician with appropriate device-specific identification information and management guidance. The core identification algorithms are based on feature extraction and matching, discrimination, statistical, and syntactic approaches. The software consists of multiple modules, including graphical input, feature extraction and selection, pattern recognition, and decision making trees as well as an external database which provides IMD specific information and recommendations.

An implanted medical device (IMD) is a medical device that is partly or totally surgically inserted into the human body or a natural orifice and is expected to remain implanted for an extended period or may be permanent. IMDs can further be classified as either active, those that use electricity, or passive, those that do not use electricity. In the US, medical devices are regulated by the FDA and classified into three classes, on basis of risk and the level of regulatory control that is necessary to assure the safety and effectiveness: class I, class II, and class III. Class III devices include devices that generally affect the functioning of vital organs and/or life support systems with very high health risk if the device were to malfunction. Because they are the most critical, the disclosure and software prototype focus on class III IMDs, although in general the embodiments disclosed herein may also address class I and class II devices.

Another aspect of the present disclosure is the construction and integration of an IMD database that can deliver updated IMD information, suggested courses of clinical management/action, and contraindications that works dynamically with the client software and patient care. The nature and form of the information allows a user to leverage the use of pattern matching algorithm data and clinical information, not only to update models but also to create new models and algorithms to rapidly detect malfunctioning, mal-positioning, and structural integrity problems (disconnections, cracks etc.) of IMD.

A still further embodiment of the present disclosure involves the compilation of data from medical images and the related IMDs. In this embodiment, clinical information regarding particular IMDs are collected and presented for analysis, where multiple occurrences of same/similar clinical situations may indicate to clinicians and manufacturers of IMDs need for recall or reprogramming modifications of the particular IMDs. For example, statistical triggers may be determined and the database analyzed for the presence of triggering situations. Once triggered, the IMD manufacturer may be presented data that suggests need for alternate placement of IMDs, recall of IMDs, or areas of special concern regarding the IMD structural integrity. Thus, the IMD manufacturer is provided with another/instant form of clinical feedback to improve upon the design, programming, use, and/or performance monitoring of its IMDs.

In another aspect, a method is described for identifying IMDs and providing context useful, often specifically adjusted to physicians, information regarding the specific IMD. Other aspects include quick identification of the IMD, and provision of clinically relevant information about the IMD to physician in a user friendly manner. This will also include a possibility to access complete and comprehensive technical information, most common reasons for the device failure or problems, common structural integrity problems of the particular device, samples of radiological images of the intact device, and selected papers from the medical literature related to specific IMD.

Further embodiments provide analysis of the structural integrity of the IMD which may impact the treatment strategy/clinical course for a particular patient. More precisely, the software will be able to indicate to radiologist any points of structural integrity problems; i.e.: disconnections of the leads, wire cracks, casings cracks, etc.

Further aspects of the present disclosure involve the compilation of data relating to the recognition and analysis of IMDs in patients. Data mining techniques may be used on the compiled data to help draw inferences regarding the use of the IMDs in populations of the IMD users.

A machine-readable program storage device is used for storing encoded instructions for a method of IMD recognition, information provision, and data compilation and analysis according to the foregoing methods.

According to another aspect, the present disclosure addresses the problem of detecting RSFOs in radiological diagnostic images (including X-ray, MRI, CT scans, and/or ultrasound) relating to a surgical area. Embodiments include at least one database containing imaging information relating to how surgical instruments appear at different plan views. Some embodiments include plan views of needles, sponges, and other instruments used during a surgical procedure. The detection software includes core algorithms based on geometric hashing, along with feature matching, statistical, and syntactic approaches so that when relevant plan images match that of the surgical instruments the location in the radiograph is provided to the surgical staff while the surgery is still occurring. In addition, further embodiments also analyze such detected objects for structural integrity, to thereby also detect is there are missing components of the object that should be located.

Pattern recognition software/algorithms are far more efficient in the detection of the objects with the known and constant dimensions then human eye and complete this task instantaneously. Therefore, such recognition software provides more efficient (better, faster, less expensive) detection of RSFOs in comparison with the current protocols involving and qualitatively depending on radiologists and/or surgeons' judgments. In addition, the image is automatically processed to remove imaging artifacts and adjust the contrast by using specific processing algorithms that will maximize the possibility for RSFO detection. These features will lead to near instantaneous RSFO detection with both a sensitivity and specificity >99. Furthermore, this software also provides near instantaneous detection of the 3D RSFOs' position/location within the operative field in a series of X-ray images once the RSFO has been identified.

Additional features and advantages of the disclosure will become apparent to those skilled in the art upon consideration of the following detailed description of the illustrated embodiment exemplifying the best mode of carrying out the invention as presently perceived. It is intended that all such additional features and advantages be included within this description and be within the scope of the disclosure.

BRIEF DESCRIPTION OF THE DRAWINGS

The above mentioned and other features and aspects of the disclosure, and the manner of attaining them, will become more apparent and the disclosure itself will be better understood by reference to the following description of an embodiment of the disclosure taken in conjunction with the accompanying drawings, wherein.

Figure 1:
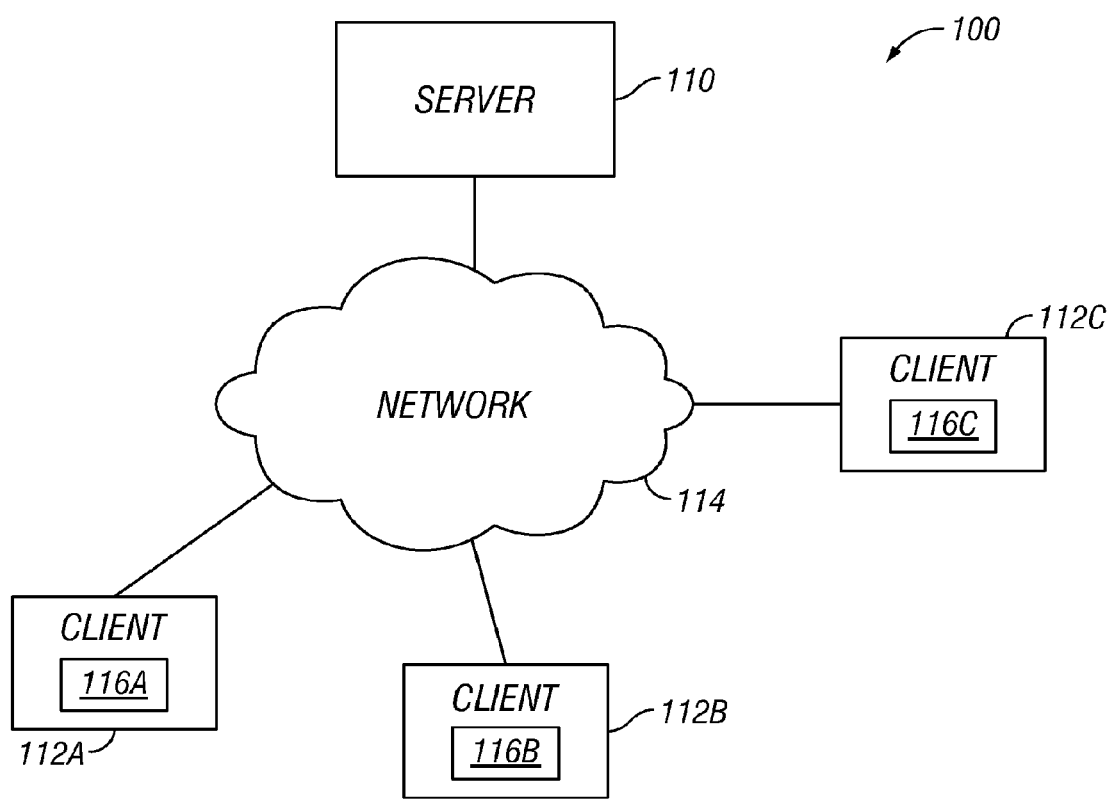
FIG. 1 is a schematic diagrammatic view of a network system in which disclosed embodiments are utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DETAILED DESCRIPTION

The embodiments disclosed below are not intended to be exhaustive or to limit the scope of the disclosure to the precise form in the following detailed description. Rather, the embodiments are chosen and described as examples so that others skilled in the art may utilize their teachings.

The detailed descriptions which follow are presented in part in terms of algorithms and symbolic representations of operations on data bits within a computer memory representing alphanumeric characters or other information. A computer generally includes a processor for executing instructions and memory for storing instructions and data. When a general purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart or manifest a physical organization on the information stored in memory. More than mere abstraction, the data structures are specific electrical or magnetic structural elements in memory which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present invention; the operations are machine operations. Useful machines for performing the operations of the present invention include general purpose digital computers or other similar devices. In all cases the distinction between the method operations in operating a computer and the method of computation itself should be recognized. A method and apparatus are disclosed for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

An apparatus is disclosed for performing these operations. This apparatus may be specifically constructed for the required purposes or it may comprise a general purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipments through signals configured to particular protocols which may or may not require specific hardware or programming to interact. In particular, various general purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system can be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms which are used frequently have specialized meanings in the present context. The term "object" relates to a set of computer instructions and associated data which can be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a world wide network of computers, namely the "World Wide Web" or simply the "Web". Examples of Browsers compatible with the present invention include the Internet Explorer® program sold by Microsoft Corporation (Internet Explorer® is a trademark of Microsoft Corporation), the Opera® Browser program created by Opera® Software ASA, or the Firefox® browser program distributed by the Mozilla Foundation (Firefox® is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information which is formatted in a Standard Generalized Markup Language ("SGML") or a Hyper Text Markup Language ("HTML"), both being scripting languages which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an extensible Markup Language ("XML") file, with XML files being capable of use with several Document Type Definitions ("DTD") and thus more general in nature than SGML or HTML. The XML file may be analogized to an object, as the data and the style sheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data (CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system which allows for application programs to be implemented on a mobile device such as a mobile telephone or PDA. Examples of Mobile Software are Java® and Java ME® (Java and JavaME are trademarks of Sun Microsystems, Inc. of Santa Clara, Calif.), BREW® (BREW® is a registered trademark of Qualcomm Incorporated of San Diego, Calif.), Windows Mobile® (Windows® is a registered trademark of Microsoft Corporation of Redmond, Wash.), Palm OS® (Palm® is a registered trademark of Palm, Inc. of Sunnyvale, Calif.), Symbian® OS (Symbian® is a registered trademark of Symbian Software Limited Corporation of London, United Kingdom), ANDROID® OS (ANDROID® is a registered trademark of Google, Inc. of Mountain View, Calif.), and iPhone® OS (iPhone® is a registered trademark of Apple, Inc. of Cupertino, Calif.), and Windows Phone 7. "Mobile Apps" refers to software programs written for execution with Mobile Software.

"PACS" refers to Picture Archiving and Communication System (PACS) involving medical imaging technology for storage of, and convenient access to, images from multiple source machine types. Electronic images and reports are transmitted digitally via PACS; this eliminates the need to manually file, retrieve, or transport film jackets. The universal format for PACS image storage and transfer is DICOM (Digital Imaging and Communications in Medicine). Non-image data, such as scanned documents, may be incorporated using consumer industry standard formats like PDF (Portable Document Format), once encapsulated in DICOM. A PACS typically consists of four major components: imaging modalities such as X-ray computed tomography (CT) and magnetic resonance imaging (MRI) (although other modalities such as ultrasound (US), positron emission tomography (PET), endoscopy (ES), mammograms (MG), Digital radiography (DR), computed radiography (CR), etc. may be included), a secured network for the transmission of patient information, workstations and mobile devices for interpreting and reviewing images, and archives for the storage and retrieval of images and reports. When used in a more generic sense, PACS may refer to any image storage and retrieval system.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown). For example, a PACS system may be set up as a server in such an arrangement, and radiographic imaging devices and/or user computing devices may be clients.

Figure 2:
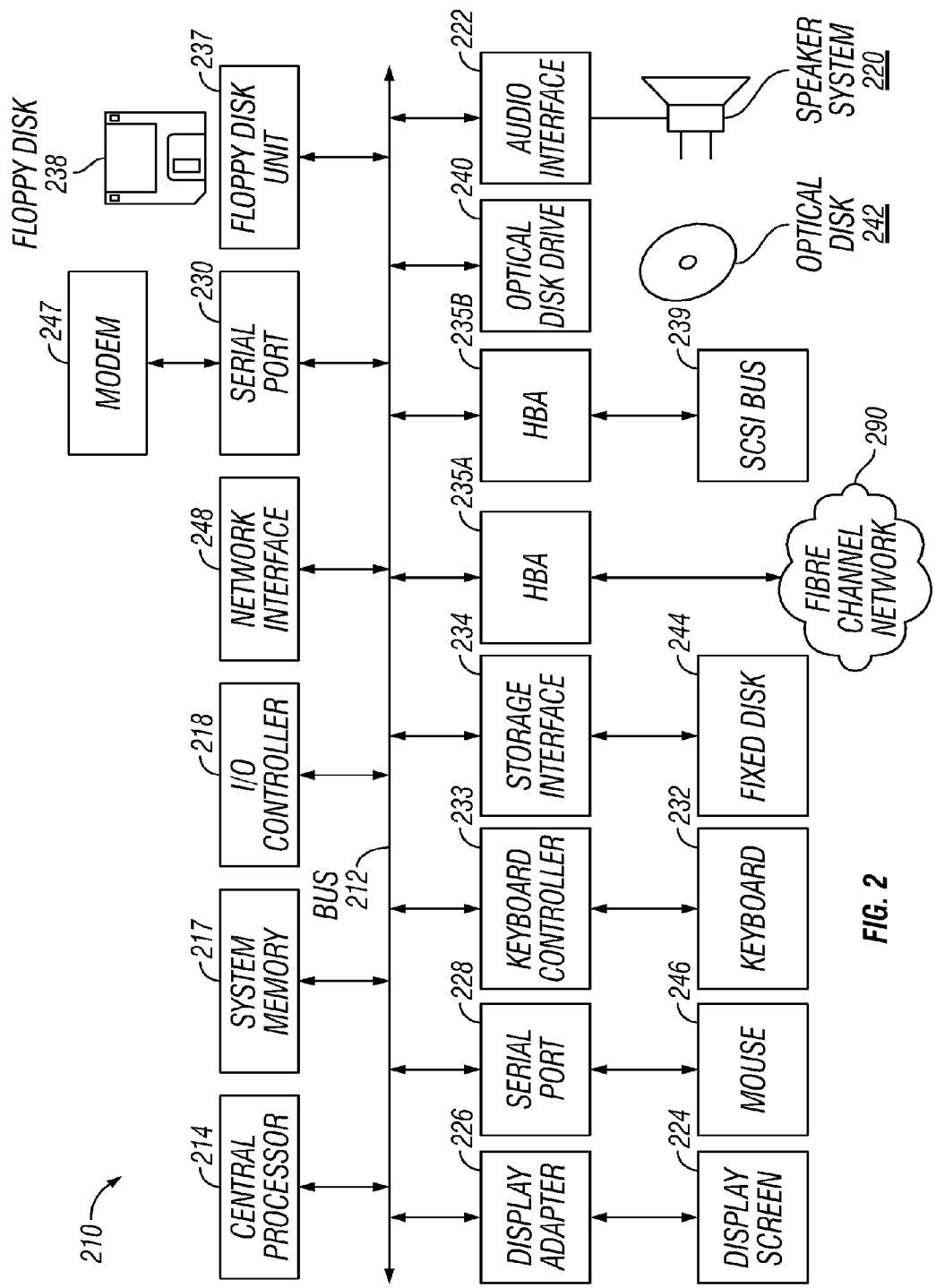
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS) which controls basic hardware operation such as interaction with peripheral components. Applications resident with computer system 210 are generally stored on and accessed via computer readable media, such as hard disk drives (e.g., fixed disk 244), optical drives (e.g., optical drive 240), and disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). For example, digital cameras of mobile devices may be also used to acquire any of the diagnostic medical images either directly from the screens (devices not connected to a network) or from the x-ray viewer and export them to the system. Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system. In some embodiments, computer system 210 may take the form of a tablet computer, typically in the form of a large display screen operated by touching the screen. In tablet computer alternative embodiments, the operating system may be iOS® (iOS is a registered trademark of Cisco Systems, Inc. of San Jose, Calif., used under license by Apple Corporation of Cupertino, Calif.), Android® (Android is a trademark of Google Inc. of Mountain View, Calif.), Blackberry® Tablet OS (Blackberry is a registered trademark of Research In Motion of Waterloo, Ontario, Canada), webOS™ (webOS is a trademark of Hewlett-Packard Development Company, L.P. of Texas), and/or other suitable tablet operating systems.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 3:
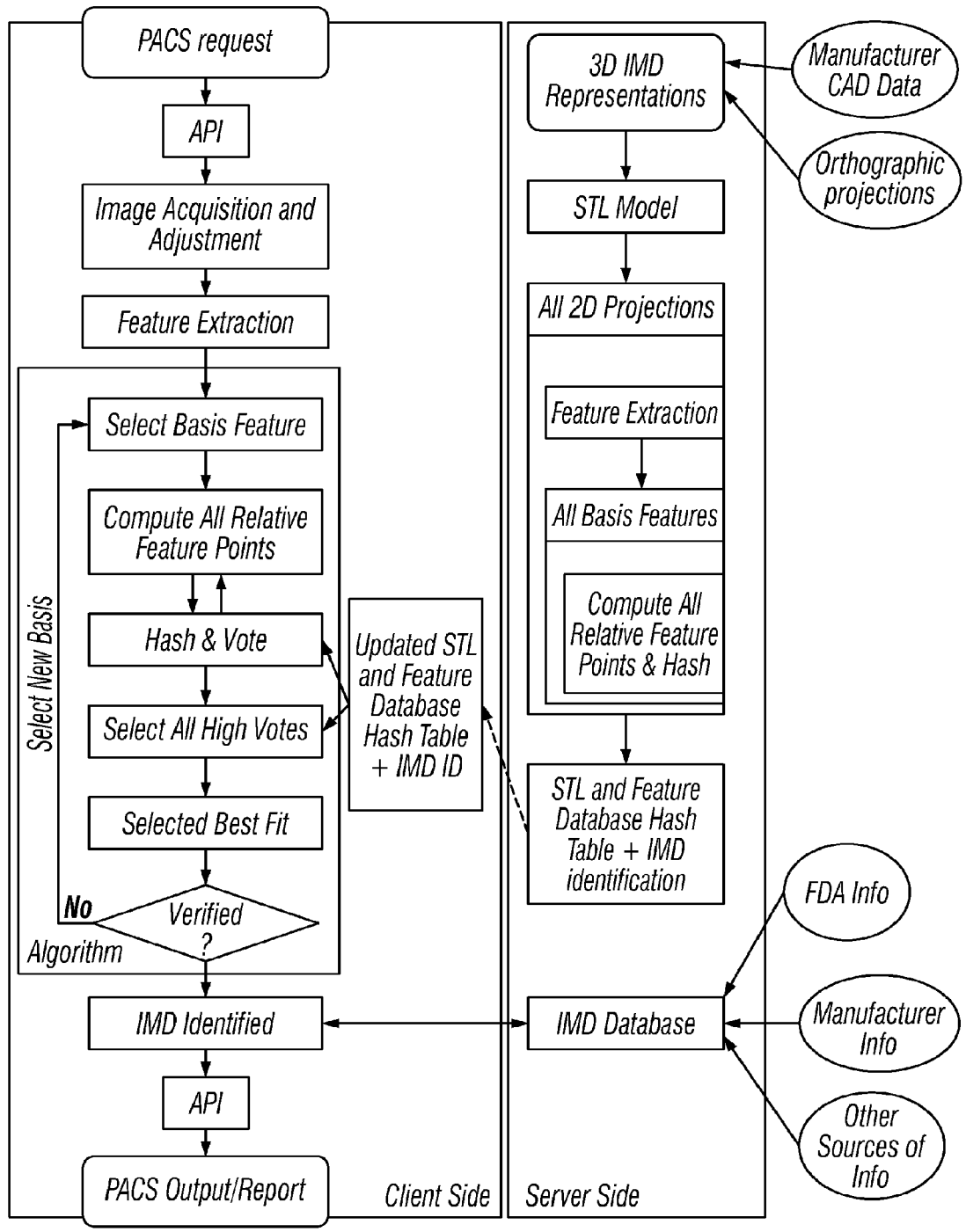
FIG. 3 is a schematic diagrammatic view showing the interaction of IMD recognition software in a system having a conventional PACS environment.

FIG. 3 shows one embodiment of identifying IMDs, which in this example is part of an enterprise PACS implementation.

Figure 4:
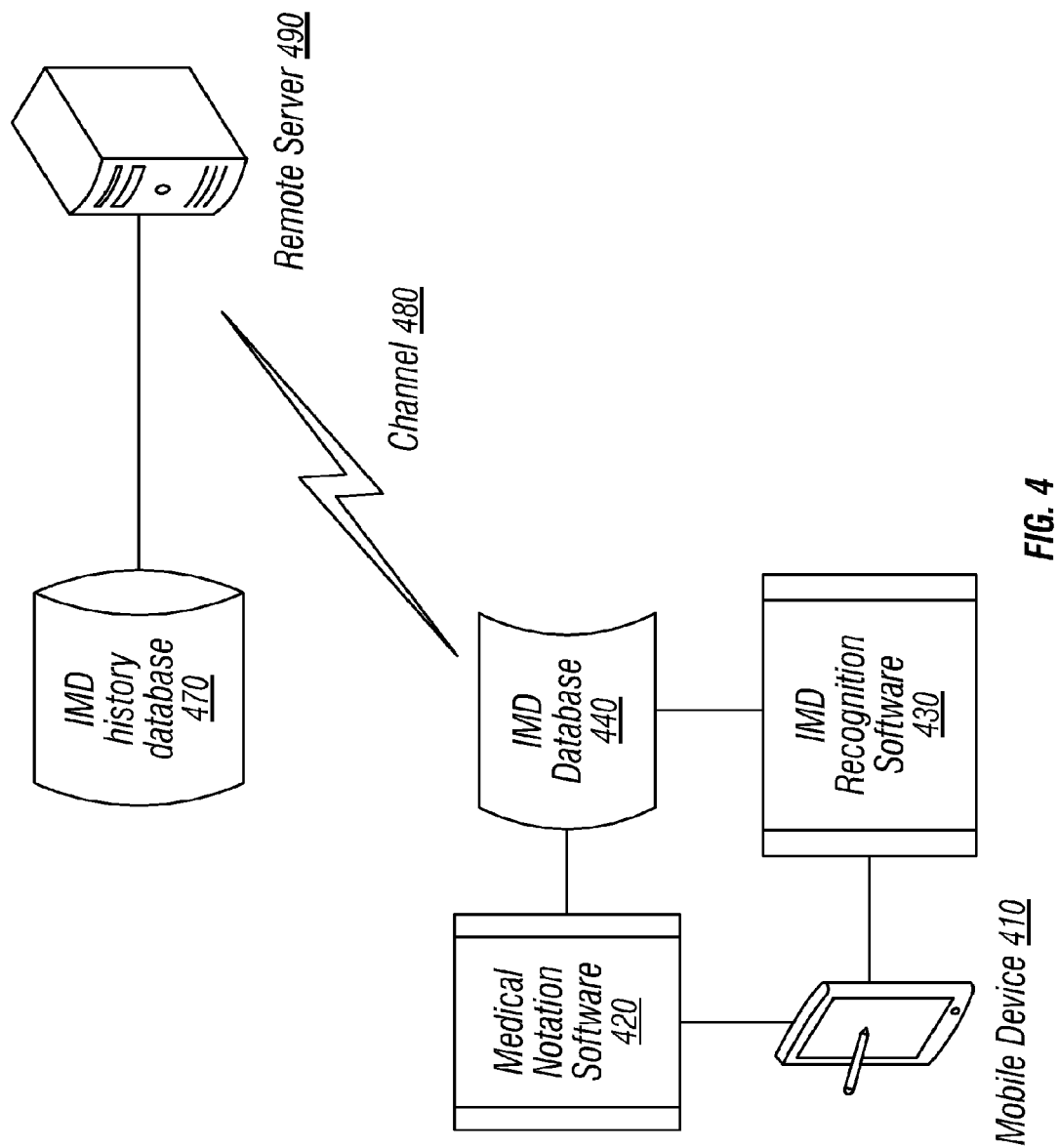
FIG. 4 is a schematic diagrammatic view showing an alternative system arrangement.

FIG. 4 shows another embodiment of the disclosure being implemented around a mobile computing device. A physician (not shown) may use mobile device 410 to enter and obtain information about a patient (also not shown). Medical notation software 420 may include both information entry and information retrieval functions, from simple textual data to complex imaging and electronic health record ("EHR") information. With this embodiment of the invention, medical notation software includes an imaging component that may obtain a medical image from an imaging device (e.g., x-ray, MRI, CT, US, or other device) by a direct communications cable, a wireless connection, or a network connection to an image from an EHR or a PACS system. Mobile device 410 also includes IMD recognition software 430, which operates on an image to analyze and identify IMDs that may be present on the image. Once identified, IMD recognition software 430 obtains further information on the identified IMD. This further information may be displayed to the physician on device 410 and/or sent to other individuals (e.g., the anesthesiologist, the imaging technician, the surgeon) to assist in the planning for diagnosis and/or treatment of the patient. This further information may be stored in IMD and/or RSFOs (such as surgical instruments, needles, radiopaque markers of the sponges, etc.) database 440, which may be stored on mobile device 410 (if it has sufficient memory), on remote server 490 (accessible through a link or telecommunications channel 480), or partially stored on a combination of mobile device 410 and remote server 490. IMD recognition software 430 may additionally create one or more new data entries into IMD history database 470 (which may be alternatively stored locally on device 410 or externally on remote server 490) with related clinical history, structural integrity, or treatment history information for use in the individual's EHR (e.g., so that IMD information [specific model and manufacturer] is automatically included in the patient's radiology report and EHR) or in an anonymous manner for data mining purposes in seeing trends, propensities, and/or deficiencies in the particular IMD.

IMD database 470 may be automatically updated with information from the FDA regarding notifications of IMD safety alerts and recalls. Upon recognition of a specific recalled IMD, physicians using IMD recognition software 430 may be alerted by the system and provided with warnings and suggested courses of action, so as to timely and appropriately inform, counsel, and refer the patient. The scope of the issue is not trivial; the FDA has issued safety alerts and recalls affecting more than 337,000 defibrillators since 1990. On average, 5 in 1,000 pacemakers and 21 in 1,000 defibrillators have had malfunctions resulting in replacement.

When a specific IMD is identified, it may be automatically entered into IMD database 430 along with basic medical information regarding the visit, enabling the FDA, device manufacturers, Medicare, and public health researchers to conduct post-market surveillance (under appropriate health information safeguards). Using this approach, specific IMDs may be flagged if a pattern of common complications or medical issues begins to emerge among those patients with that IMD. Furthermore, while not widely recognized and publicized, cases of IMD counterfeiting have been reported and is expected to rise. An automated recognition system coupled with the development of radio-opaque unique device identifiers (either existing or those currently being developed) contribute to the verification of genuine IMDs and ease the identification of counterfeit copies.

In addition to identification and basic information, IMD recognition software 430 may also indicate to the physician common malfunctions and complications encountered with the particular IMD in the past and provide images of its proper radiological appearance. This facilitates the diagnostics of the structural integrity issues including wire cracks, loosening of connectors, or disconnections of IMDs which will be possible in some embodiments by the software itself.

Pattern recognition software is a rapidly developing field; examples range from the simple, such as reading bar codes, to the extraordinarily difficult, such as voice recognition, automatic recognition of objects, or specific individuals identified from photographs or live streaming aerial 2D or 3D videos. Image analysis is largely based on techniques/algorithms for pattern recognition, which refers to detection of meaningful patterns in raw image data. This technology is widely used in consumer devices (smart phones, digital cameras), computers (scanning and optical character recognition), security (fingerprint and iris identification), defense (target recognition and tracking via satellite imagery) and numerous other fields and industries (metallurgy, robotics, microscopy, medicine, etc.).

IMDs and RSFOs are therefore three dimensional ("3D") physical objects implanted or unintentionally retained in patients' bodies. Broadly, they are usually made of biocompatible metal alloys such as IMDs (e.g., pacemaker, defibrillators, ventriculo-peritoneal shunts, spinal cord stimulators, etc.) and surgical instruments or different surgical fabric materials, such as sponges, gauze towels, and laparotomy pads that contain radiopaque markers—potential RSFOs.

Because the density of these materials, e.g. pacemakers, needles, sponges, etc., is generally different than that of the tissue, RSFOs and IMDs are visible on medical images (e.g., X-ray, ultrasound, MRI, and/or CT images). Data obtained in virtually all medical imaging modalities consists of two dimensional ("2D") representations of three dimensional (3D) structures, making the radiographic images obtained effectively a type of axonometric projection. It is worth noting that this is true even in certain 3D medical imaging modalities where sophisticated 3D reconstruction processing takes place after a series of multiple 2D images has been obtained. Geometrically, 2D axonometric projections are affine transformations (involving rotation, scaling and shear) and translations (shifts) of combined orthographic projections ("plan views," a collection of which makes up a complete 3D model of an object). This makes it mathematically possible to analyze a single 2D radiographic image of an RSFO and, if a 3D model of that particular object is known and available, match it to a particular model.

Figure 9A:
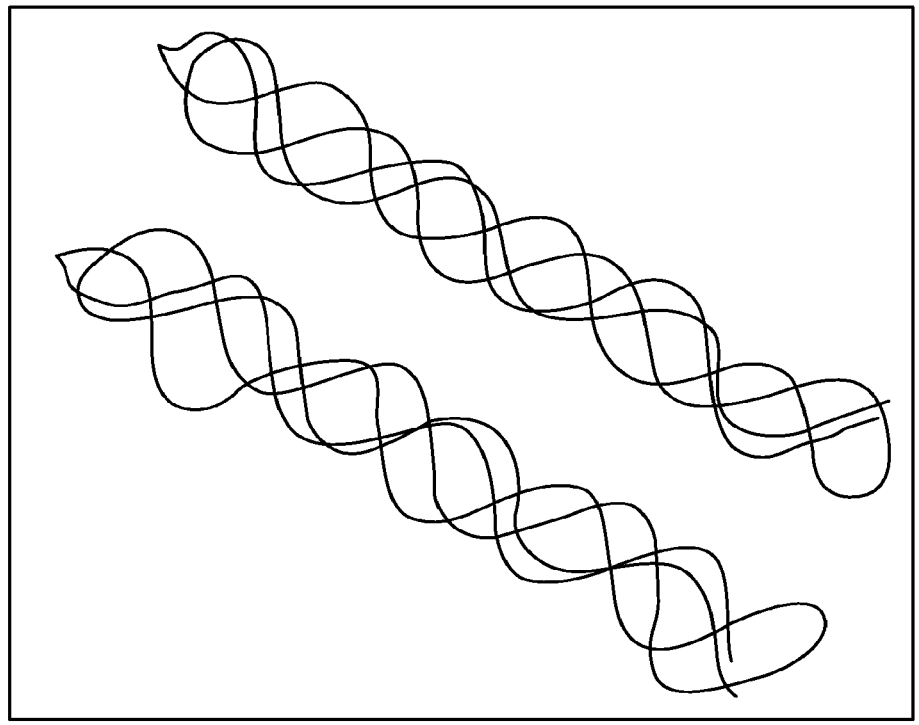
FIGS. 9A and 9B are radiographic images of sponges.
Figure 9B:
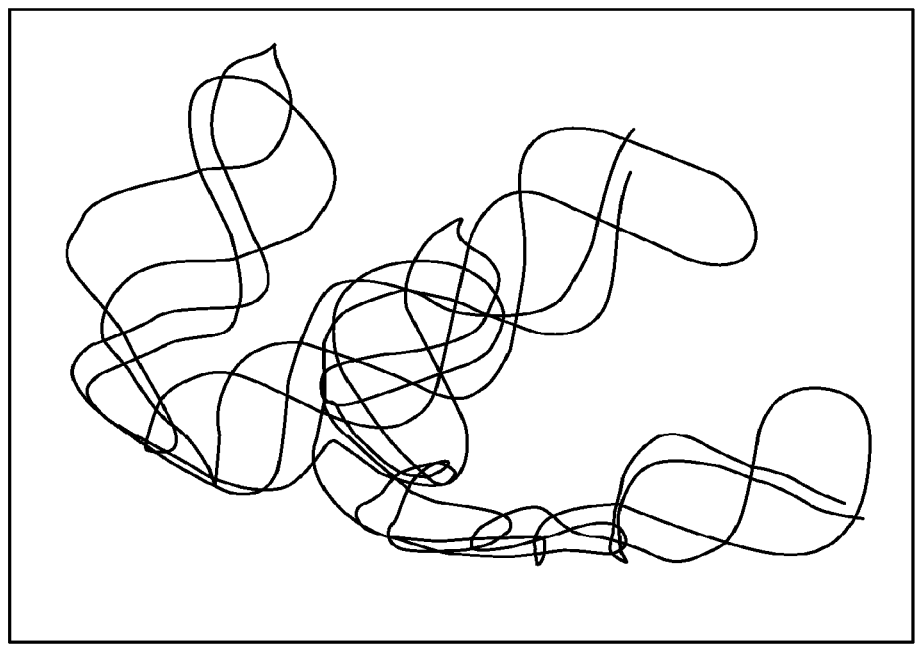

Examples of radiographs of a flat and crumpled sponge with radiopaque markers are shown in FIGS. 9A and 9B, wherein the radiograph markers of the exemplary sponges have a double helix shape. With the sponge radiographs, the definable points are the intersection points of the radiograph markers as well as characteristic inflection points, but not limited only to this feature. In addition, the radiographic lines of the markers have a known thickness, so that the orientation of the sponge relative to the radiograph may be in part determined by the thickness of the marker line on the radiograph. A 3D model of the sponge may also be generated based on the variation of marker line thickness. Such a 3D model may not necessarily precisely locate the entire sponge, because portions of each sponge do not contain radiographic markers. However, having a known position and orientation of a sponge's radiographic marker provides an approximate zone where the remaining portions of the sponge are likely to be located.

Figure 10C:
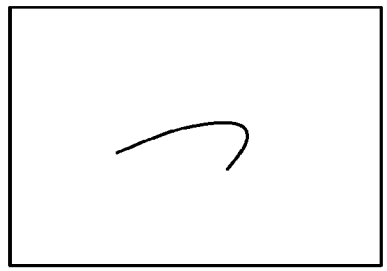
FIGS. 10A-10C are radiographic images of needles.
Figure 10B:
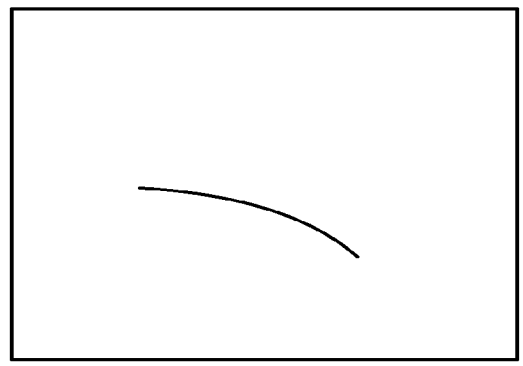
Figure 10A:
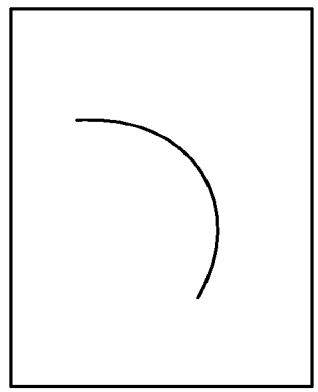

Examples of needle radiographs are in FIGS. 10A-10C wherein a generally arc shaped needle may appear straight, slightly bent, or as a true arc depending on the plan view. In addition to radiographic projections, in some embodiments models of the structure of each potential needle are included in the pattern recognition. In these embodiments, the structural integrity of the needle may be evaluated against the radiographic image. This allows for the display to indicate not only the position of a needle in the surgical site but additionally may indicate if needle is partially bent or broken—important information for the retrieval of the needle. A bent needle may need to be removed in a non-standard procedure, and a broken needle may indicate that the surrounding tissue should be inspected for possible needle fragments. In some embodiments of the invention, the pattern recognition software generates projections of the missing portion(s) of a needle and searches the radiograph for the corresponding piece(s).

Pattern recognition algorithms have not been extensively used in the analysis of the diagnostic radiological images. The utility of the pattern recognition algorithms/technology to the specific problem of IMDs and RSFOs identification and detection is remarkable. Such pattern recognition software provides more accurate (sensitivity and specificity >95) and faster/instantaneous identification of IMDs and RSFOs detection in medical diagnostic images (CT, X-ray, MRI, ultrasound) than current protocols (sensitivity and specificity <60) that take 30-40 minutes for completion. This is crucial in the emergent situations when a patient in the OR is not stable and where prolongation of anesthesia until the RSFO is detected or ruled out carries the significant risk or when newly admitted patient with IMDs in emergency room need an urgent diagnostics or therapeutic procedures which cannot be started until the EVID is identified.

Envisioned integration of the pattern recognition software into PACSs and/or portable X-ray machine software environments through their application programming interfaces (API) makes this software widely applicable in everyday clinical practice. Proposed pattern recognition software directly translates computational technologies and software algorithms into clinical practice and solves emerging clinical problems in an efficient manner. Pattern recognition software is a rapidly developing field, examples of which range from simple, such as reading bar codes, to extraordinarily difficult, such as voice recognition, automatic recognition of objects, or individual people identification from photographs or live streaming aerial videos. Image analysis is largely based on algorithms for pattern recognition, which refers to detection of meaningful patterns in raw image data. This technology is widely used in consumer devices (smart phones, digital cameras), computers (scanning and optical character recognition), security (fingerprint and iris identification), defense (target recognition and tracking via satellite imagery) and numerous other fields and industries (metallurgy, robotics, microscopy, medicine etc.)

Some embodiments of the disclosure for the identification of IMDs and detection of RSFOs from the X-ray or CT images and/or any other type of diagnostic imaging are based on pattern recognition algorithms. Software modules for graphical input analysis, feature selection and extraction, pattern recognition based on two dimensional ("2D") axonometric projections of the three dimensional ("3D") models of RSFO, and decision making based on feature matching, statistical, and syntactic approaches are included. Specific algorithms best suited for the EVID identification and/or RSFO detection from single 2D radiographic image or from multiple such images are used. More precisely, feature extraction methods include, but are not limited to, edge detection, interest point detection including Harris, Kadir-Brady, Difference of Gaussians, Harris-Laplace, Maximally Stable Extremal Region detectors, and other interest point detection methods. Methods for recognition of objects based on known 3D models include, among others, parametric and generalized Hough transforms, geometric hashing, implicit shape models and other voting-based methods. Recognition by parts includes, among others and in addition to variants of methods mentioned above, constellation models, poselets, pictorial structure methods, 2D and 3D deformable parts models, grammar and topic models. Appearance-based methods include, among others, template matching, edge matching with Chamfer and distance transforms, active contours, medial axis matching, gradient matching, and correlation based matching. Feature representations used in any of the above methods may include, among others, shape contexts, scale-invariant feature transform, speeded up robust features, histograms of oriented gradients, local binary patterns. Some embodiments of the disclosure are primarily based on edge detection, gradient matching, normalized cross-correlation and kernel density estimation, but not limited to any particular algorithms/methods as we may use other above mentioned algorithms/methods. All the above mentioned algorithms may alternatively be used in certain situations. These algorithms are further combined with probabilistic ranking and hypothesis testing, perceptual organization, and spatial correspondence algorithms for recognition from single 2D radiographic image. Such recognition is made possible by generating a plurality of projections for each possible object, so that the three dimensional object does not need to be identified—only one of the representative two dimensional projections need be identified. In some cases, embodiments are based on normalized cross-correlation methods/algorithms.

Again, the mathematical methods and algorithms used in image analysis and pattern/object recognition are described and available. Recognition of objects based on known computer-aided design ("CAD") 3D models include, but are not limited to, edge detection, primal sketch, Man, Mohan and Nevatia, Lowe, and Faugeras methods. Recognition by parts includes Binford, Biederman, Dickinson, Forsyth and Ponce methods. Appearance-based methods include edge matching, divide-and-conquer search, grayscale matching, gradient matching, and large model bases systems. Feature-based methods include interpretation trees, hypothesize and test, pose consistency, pose clustering, invariance, geometric hashing, scale-invariant feature transform ("SIFT"), speeded up robust features ("SURF") and Harris corner detector ("HCD"). Embodiments are also contemplated that use complex approaches, including but not limited to discrimination algorithms, support vector machine, template matching, gradient histograms, inter and intra-class transfer learning, explicit and implicit 3D object models, global scene representations, shading, reflectance, texture, grammars, topic models, window-based detection, 3D cues, context, leveraging internet data, unsupervised learning, and fast indexing algorithms.

Thus, in some embodiments, a database of 3D models or multiple images of IMDs or RSFOs (e.g., surgical instruments, needles, and radio-opaque markers of sponges, gauze towels, and/or laparotomy pads) is the starting point. However, this disclosure is not limited to this approach. Using these 3D models or image archives, a database of their specific extracted features or axonometric projections is generated for a plurality of axiomatic 3D orientations. Existing CAD files (for example, provided by manufacturer and/or Food and Drug Administration) may be used to create the database, or alternatively new data base files may be created using, for example, a 3D scanner or compiling series for their X-ray/CT scan images. Specific axonometric projections or specific selected features may be used by the system for IMDs and/or RSFO comparison and subsequent recognition in medical images, such as X-rays or CT scans.

In some cases, the identification of IMDs and detection of RSFOs may require a specific selection and arrangement of known techniques in particular ways. The recognition software utilizes, but is not be limited to only using these algorithms or their derivatives. The herein described algorithm is only one of the possibilities that we utilized for recognition of IMDs or RSFOs detection on massive scale.

Again, IMDs and RSFOs are three dimensional physical objects implanted into patients' bodies. Broadly, they are made of biocompatible metal alloys, plastics and various other polymers. Because the densities of these materials are generally different than that of tissue, IMDs are visible on virtually all medical imaging modalities.

Data obtained in nearly all medical imaging modalities typically includes 2D representations of 3D structures, making the radiographic images obtained effectively a type of axonometric projection. This is true even in certain 3D medical imaging modalities, where sophisticated 3D reconstruction processing takes place after a series of multiple 2D images has been obtained. Geometrically, 2D axonometric projections are affine transformations (involving rotation, scaling and shear) and translations (shifts) of combined orthographic projections ("plan views," a collection of which makes up a complete 3D model of an object). This makes it mathematically possible to analyze a single 2D radiographic image of an IMD and, if a 3D model is known and available, match it to a particular model.

Pattern recognition algorithms may be created based on graphical input analysis and RSFO feature selection/extraction relaying on their comparison with the axonometric projections or image specific features data bases. Thus, for a particular set of objects, an optimized pattern recognition algorithm may be employed. Alternatively, a database of a universal set of objects may be created, and a more generalized pattern recognition algorithm may be used. For the purpose of having a fast algorithm that may identify IMD or detect potential RSFO's while a surgery is still in progress, it may be advantageous to start with a limited set of objects and an optimized pattern recognition algorithm. In one exemplary embodiment, such an optimized pattern recognition algorithm was developed to have as criteria for acceptance: Achieving >95 sensitivity and specificity for identification of the two IMDs in the plain orthogonal (rotation only around z-axes) X-ray images and >95 sensitivity and specificity for detection of the two RSFOs (surgical needle and radio opaque marker of surgical sponge) in any given projection angle (3D/rotation in all three axes). Current software prototype are developed in MATLAB (Math-Works™, Natick, Mass., USA) and capable of recognizing SynchroMed II Programable Drug Infusion System (Medtronic, Minneapolis, Minn., USA) and Itrel 3 Neuro stimulator (Medtronic, Minneapolis, Minn., USA) spinal cord stimulator in different orthogonal XRs images exported from the PACS environment; e.g., (2D/device rotated only around z-axes with fixed x- and y-axes). In another exemplary embodiment of the present invention—the proof of principle has been also developed in MATLAB (Math-Works™, Natick, Mass., USA) capable indentifying Accu-Sorb X-Ray Detectable USP Type VII Gauze (Medline Industries Inc., Beijing, China) radiopaque marker and 2-0 SS-695 Wax coated 3 Metric ⅜, 24 mm cutting needle (Syneture-Covidien, Mansfield, Mass., USA) from X-ray images in any given projection (3D/objects rotated around all there axes).

In other embodiments, the 3D model/axonometric projections database of IMDs and all RSFO may be expanded to include all FDA approved IMDs and potential RSFOs— surgical tools (small size instruments in standard OR sets), needles, and surgical materials' radio-opaque markers of the sponges and laps. The pattern recognition algorithms for recognition of these objects may be further refined and evaluated in a similar manner to that described above.

In another embodiment, the pattern/object recognition and database-access algorithms are implemented in a Visual C++ software environment (Microsoft, Redmond, Wash., USA) and a widely available cross-platform relational database management system is used to host the database (such as MySQL Enterprise, Microsoft SQL Server, or Oracle Database Enterprise).

Further embodiments may be developed and their accuracy tested by using historical image data and object usage data. For a particular surgical location, or even a particular type of surgery, patients may be identified with multiple intra-operative X-ray images and/or history of IMDs or RSFOs in the particular PACS/digitalized medical record system. These medical records may be mined and subjects with the history of IMDs and/or RSFO or multiple intra-operative X-rays (which still may be used for testing/ identification or visible surgical instruments) are selected and their X-ray images downloaded to a database (cleared for any personal health information). The pattern recognition algorithms developed for other locations and/or types of surgery/IMDs and/or RSFOs may then be tested. Particular algorithms and mode performance may be adjusted to achieve optimal and instantaneous identification with overall >95 sensitivity and specificity in real patient images.

Embodiments of pattern recognition software of the invention may be integrated into PACSs and/or portable X-ray machine software environments as a tool menu, such as an addon program, an additional pull-down/drop down menu, or a sub-menu option within the PACS system software environment. In one embodiment, a software application programming interface ("API") of the PACS or portable X-ray machine software is used to integrate the pattern recognition software. All major PACS and portable X-ray machines software packages/user environments contain an API, which enables them to interface with other software systems. They are able to output data to a third-party program and receive input from other applications. In most of the PACS this is accomplished through the introduction of third-party toolboxes/drop down tool menus, which may be implemented in several embodiments of the invention. Upon activating the pattern recognition software through a toolbar available in the PACS or portable X-ray machines software environment, a radiographic image is sent to the pattern recognition software that adjusts and analyzes the image using pattern recognition algorithms— essentially comparing the encountered 2D representation to the 2D axonometric projections (or any specific features) database of known 3D models of IMDs and/or RSFOs. Ideally, the pattern recognition database would contain axonometric projections or specific features of the 3D models of all FDA approved IMDs and/or potential RSFOs including surgical instruments, needles, and radio-opaque markers of surgical materials.

Pattern recognition software/algorithms are far more efficient in the detection of objects with the known and constant dimensions then human eye and complete this task instantaneously. Therefore, such software provides more efficient (better, faster, less expensive) identification of IMDs and faster detection of RSFOs in comparison with the current protocols. In addition, the image is automatically processed to remove imaging artifacts and adjust the contrast by using specific processing algorithms that maximize the possibility for IMD identification and/or RSFO detection. These features lead to near instantaneous IMD identification and/or RSFO detection with both a sensitivity and specificity approaching 99% with current software prototype. The pattern recognition software shortens the time for the IMDs identification and/or RSFOs detection in radiological images. In addition, it also provides information summary specifically needed by physician on specifically identified IMD and, if needed, more comprehensive manufacturer's manual and scientific publications related to specific device. Furthermore, envisioned software provides near instantaneous detection of the 3D RSFOs' position/location within the operative field in a series of X-ray images once the RSFO has been detected.

Figure 6:
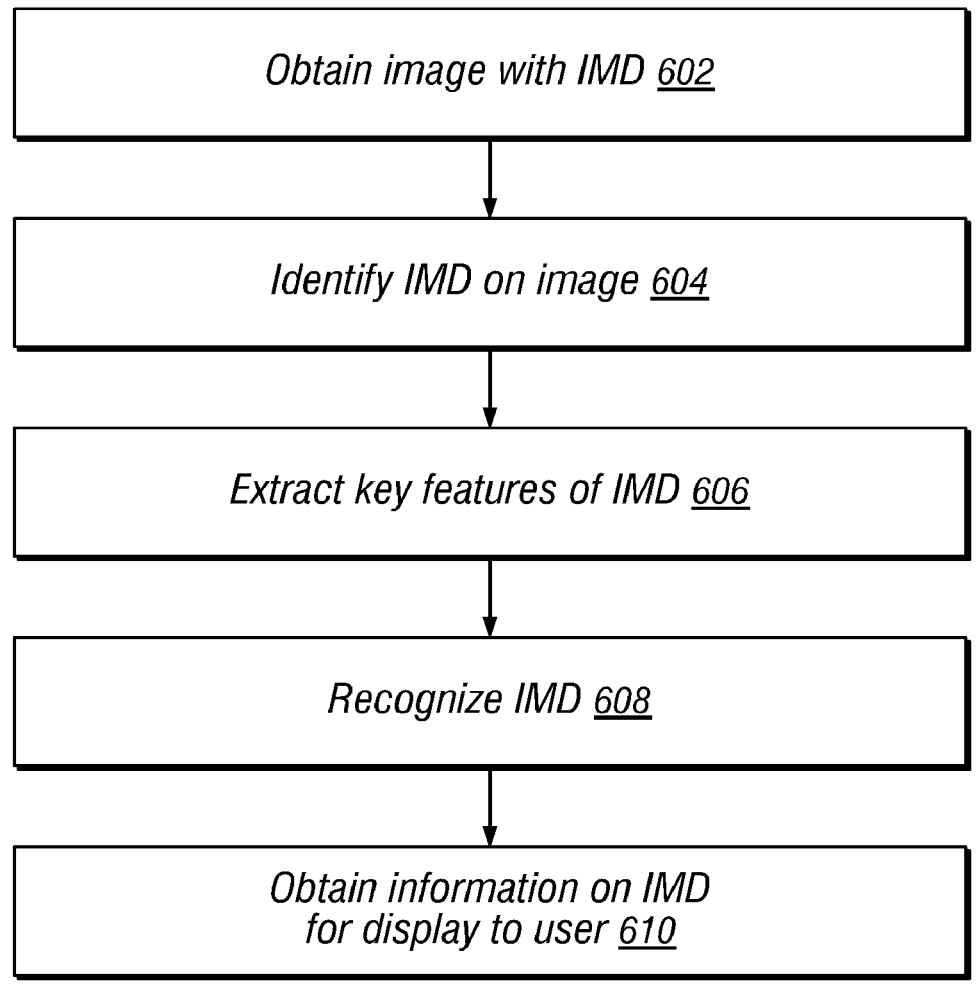
FIG. 6 is a flow chart diagram relating to the operation and use of an embodiment of the present disclosure.

FIG. 6 shows an example process that could be used by the system in conjunction with an IMD. In this example, an image with an IMD is obtained (step 602). The IMD on the image is identified (step 604) and key features extracted (step 606). The IMD is recognized based on the IMD database (step 608). Information about the IMD, such as instructions, safety information, and/or recalls, could be displayed for the user (step 610).

In some embodiments, in the cases when RSFO is identified, additional projections/portable X-rays are usually necessary to approximate the position of the RSFO in the surgical field. This is particularly relevant in emergent abdominal or chest surgeries that have relatively large operative fields. Therefore, by rapidly identifying the RFSOs in different projections, this software will also significantly shorten the time needed to locate the RSFO within the surgical wound/field.

This concept is particularly important in the case of the RSFOs since overall effectiveness of intra-operative radiographs in detection of RSFOs is limited by the spatial resolution sensitivity and specificity of the human eye, decline of concentration, quality of communication between the OR team and radiologist, quality of X-ray images, subjectivity of the surgeon or radiologist, and lack of their formal training in recognizing RSFOs. In the same way, the identification of IMDs is greatly limited by the already high and constantly expanding number of different devices on the market. Pattern recognition software/algorithms are far more effective in the detection of the objects with the known and constant dimensions and complete this task nearly instantaneously. Furthermore, the image is processed to remove imaging artifacts and adjust the contrast using appropriate algorithms that will maximize the possibility for the correct IMD identification and RSFO detection. Therefore, this software/advisory tool greatly increases IMD identification and RSFO detection sensitivity and specificity and shortens the time of x-ray image analysis.

In the event of an incorrect needles, sponges, and or surgical instruments count—potential RSFO—(counting is mandatory before the completion of the surgery according to current practice) the portable X-ray of the operative field should be made available to the radiologist within 20 minutes while the radiologist evaluation/confirmation to the surgeon in the OR should be completed within another 20 minutes. On average this entire process takes approximately 30-40 minutes. Embodiments of the inventive pattern recognition software significantly shorten this time. This is crucial if the patient is unstable in the operating room. Furthermore, this also shortens the operating room time, anesthesia time, and all the associated risks.

In one embodiment, the pattern/object recognition and database-access algorithms are written in Visual C++ (Microsoft, Redmond, Wash., USA) and a widely available via a cross-platform relational database management system (RDBMS) (such as MySQL Enterprise, Microsoft SQL Server, or Oracle Database Enterprise).

Pattern recognition software development and optimization may be programmed using Visual C++ or a plurality of other computer languages. As previously explained, embodiments are contemplated in which 2D contours of RSFOs and/or IMDs on radiographic images are analyzed as axonometric projections of 3D models of the IMDs or potential RSFOs—surgical instruments, needles, and radioopaque markers of surgical materials that have undergone affine transformations, which preserve certain relationships between physical points, for example, parallelism between the edge lines is maintained. This forms the basis for the approach taken in the existing embodiments of the invention that rely in normalized cross-correlation. This approach was used in both developed software prototypes—IMDs identification and RSFOs detection. However, the present disclosure is not limited to this approach and may include methods and approaches or their combinations as mentioned previously.

There are two phases in this approach: (1) the preprocessing phase, in which the models for the objects to be detected/identified are built, and (2) the recognition phase applied to novel images.

The preprocessing phase only needs to take place once for every type of object to be recognized by the software (an IMD or an RSFO). The goal of this phase is to construct representation of the object that can be used by the recognition algorithm. This may include collection of a tightly cropped view of the object from a variety of viewpoints covering a range of out-of-plane rotations; in-plane rotations (around z-axis) can be automatically and accurately generated by image warping. Multiple views of the object may be obtained by collecting a set of radiological images with the object in the scene, positioned in the desired range of poses; by rendering a set of synthetic views from a 3D model such as that generated by software like AutoCAD® (AutoCAD is a registered trademark of Autodesk, Inc., San Rafael, Calif.), or by other means. For most devices between 10 and 60 views are sufficient.

For embodiments using appearance-based methods, the desired representation is obtained by storing the multiple views as templates, after applying transformations that make subsequent recognition robust, such as contrast normalization, Gaussian smoothing, and cleanup by morphological image operation (noise removal). For embodiment using part-based methods, an additional step may involve extraction of parts represented in the same way; for embodiment using methods that combine template- and part-based approaches, such as deformable part models, the parts may be learned automatically along with the optimal placement of template window on the object in each view, from a data set of radiological images in which known locations of the object are marked. The parts may be as large as the entire object, or as small as a few square pixel sized windows with characteristic points on the object.

The second phase involves applying the representation constructed in the first stage to the input image in which IMDs and/or RSFOs must be detected and identified. In template-based recognition, the detection may rely on normalized cross-correlation between the stored object templates and the image, on response of a linear filter constructed from a training set of known locations of the object in radiological images by means of a statistical learning algorithm such as the structured support vector machine, or another mechanism that computes score of a hypothetical match between every location in the image and the stored templates. In part based methods, in addition to the mechanism described above, this may include similar computation for every part. The part scores may be combined in a shape-aware model, or, as in one existing embodiment of the invention, by means of anisotropic kernel diffusion, to contribute to the score of the regions(s) highly likely to contain the object. Finally, performing non-maxima suppression to eliminate redundant detections, and suppressing detections with match score below threshold (tuned by an automatic method with the objective to obtain the desired specificity/sensitivity), yields a (possibly empty) set of hypothesized detections.

Upon producing non-empty set of detection hypotheses, detection and identification of the object is automatically provided since it is linked to the templates generated in the first phase. Further verification phase is possible, by means of applying a statistical classification method trained on examples of radiographic images with known identity of objects (IMD or RSFO). Examples of classification techniques applicable here include logistic regression, support vector machines, boosting, and decision trees.

Another possible approach is geometric hashing. There are two distinct phases in geometric hashing algorithms: (1) the preprocessing phase, involving finding specific unique feature points in the model; and (2) analysis and recognition phase.

The preprocessing phase needs to take place only once (off-line), and may be conducted independently of real-time image analysis and the recognition phase (on-line). In the preprocessing phase, a series of steps are conducted for each object recognized. Briefly: a) A 3D model (such as generated by software like AutoCAD® (AutoCAD is a registered trademark of Autodesk, Inc., San Rafael, Calif.)) of surgical instrument, needle, or radio-opaque marker, obtained either from the manufacturer or generated by 3D scanner, is converted into stereo-lithography—triangular representation of a 3D surface geometry (STL) format which defines the geometry of an object; b) Using 360 degree cuts, two-dimensional projection scenes of the device from multiple angles and perspectives are generated; c) Using edge and corner detection algorithms, unique feature points of the device are identified on each of these planar projection images. These are the model's feature points; d) For each ordered non-collinear triplet of feature points, affine coordinates of the remaining feature points are calculated using the original triplet as a basis; e) Each of these coordinates is entered into a hash table describing the relevant basis triplet, corresponding locations of feature points and a code identifying the device in question; and f) By repeating this algorithm for each feature point basis identified on each planar projection image derived from a 3D CAD model of each device, the pattern recognition software generates an STL database which may be used to recognize RSFO in radiographic images.

In the second, recognition phase, radiographic images are analyzed in real-time to identify an EVID or RSFO in the X-ray image. The following steps are conducted: a) An input X-ray image is imported from the PACS or directly from portable X-ray machine software into the pattern recognition software, for example by using the API; b) The image is processed to remove/adjust imaging artifacts and adjust the contrast using appropriate algorithms; c) Using edge and corner detection algorithms (similar to those in the preprocessing phase), unique feature points are identified in the input image; d) An ordered, non-colinear triplet of interest feature points are arbitrarily selected in the input image. This is the arbitrary basis; e) Affine coordinates of the remaining feature points identified in the input image are calculated; f) For each such coordinate, the entire hash table contained in the external STL database is searched for a match; and g) If a sufficiently close match is identified in the hash table, a vote will be recorded for that entry. Other algorithms may use/extract different object features for detection or different process; however, the basic step/principle of comparison to the objects and extracted features in the internal/existing IMDs/RSFOs data base will remain similar.

This series of on-line real time steps is repeated for each arbitrary basis triplet identified on the input image. If sufficiently high number of votes are recorded for entries in the hash table that belong to the same surgical instrument, needle, or radio-opaque marker, it will be considered to be present in the analyzed image, and user notified. Although geometric hashing algorithms are used in this exemplary embodiment of the invention, alternatively different algorithms (mentioned above) may be used to further optimize interface with STL or other extracted image features data bases.

More precisely, evaluation and implementation of the core image detection algorithm is the initial and most complex step. Assuming usage of geometric hashing—after the software optimizes the image—the 2D contours of IMDs or RSFO on radiographic images to be analyzed are essentially axonometric projections of 3D representations that have undergone affine transformations, which by definition preserve certain relationships between physical properties of the device. Because, for example, parallelism between the edge lines is maintained, the correspondences between 2D image features and the known 3D model features (known as the model base) are not independent. These invariants, governed by geometric constraints, form the basis for geometric hashing.

Hash functions are algorithms or subroutines that map large datasets to smaller datasets. The geometric hashing is a paradigm for model-based recognition of objects. More precisely, geometric hashing algorithm precomputes invariant geometric relations of the models and uses them for recognition by identifying common substructures in a scene regardless of rotation, translation, and scale. There are two distinct phases in geometric hashing algorithms:

The first, preprocessing phase, involves finding specific unique feature points in the model. In some embodiments, this preprocessing phase needs to take place only once (offline), and is conducted independently of real-time image analysis and the recognition phase (on-line). In one exemplary embodiment of the preprocessing phase, there is a series of steps that are conducted for each device. Briefly:

a. A 3D AutoCAD (Autodesk, Inc., San Rafael, Calif., USA) model of an IMD of potential RSFO, obtained either from the manufacturer itself, FDA, or generated by using available orthographic projections of the device (obtained from manuals or other sources; i.e., 3D scanner, or directly from multiple X-ray images), is converted into a stereo-lithography format (STL), which defines the geometry of an object as a triangular representation of the 3D surface geometry in a three dimensional Cartesian coordinate system.

b. Using 360 degree cuts, two-dimensional projection scenes of the device from multiple angles and perspectives are generated.

c. Using appropriate edge and corner detection algorithms, unique feature points of the device are identified on each of these planar projection images. These are the model's feature points.

d. For each ordered non-colinear triplet of feature points, affine coordinates of the remaining feature points are calculated using the original triplet as a basis.

e. Each of these coordinates is entered into a hash table describing the relevant basis triplet, corresponding locations of feature points along with a code identifying the device in question.

f. By repeating this algorithm for each feature point basis identified on each planar projection image derived from a 3D CAD model of each device, an internal STL database is generated which is used to recognize IMDs or RSFOs in diagnostic (X-ray, CT, MRI, or ultrasound) images.

Other embodiments of the reprocessing phase are not limited only to this specific algorithm/approach.

In the second recognition phase, radiographic images are analyzed in real-time to detect and identify an IMD and/or RSFO from the images. More precisely, the following steps are conducted:

a. An input radiographic image (typically an XR or pilot CT image itself or combined with one or more cross sectional images if needed—step g. not completed) is imported from the PACS into the pattern recognition software using the API.

b. The image is processed to remove/adjust imaging artifacts and the contrast adjusted using appropriate algorithms. XR image and pilot CT scans are essentially free of such artifacts, however the cross CT sections have a significant degree of artifacts generated from the metal components of the EVIDs and/or RSFOs. Existing algorithms/software solutions (available on the market) for artifact reduction are used in these cases especially when the pilot CT scan image is insufficient for device recognition and needs to be supported by the cross sectional images.

c. Segmentation of the image and detection of RSFO or IMD image location.

d. Using the same edge and corner detection algorithms as in the preprocessing phase, unique feature points are identified in the input image.

e. An ordered, non-colinear triplet of interest feature points is arbitrarily selected in the input image. This is the arbitrary basis.

f. Affine coordinates of the remaining feature points identified in the input image are calculated. g. For each such coordinate, the entire hash table contained in the internal STL database is searched for a match.

If a sufficiently close match is identified in the hash table, a vote is recorded for that entry which subsequently provides detection of the RSFO and/or IMD with IMD identification and subsequently, by linking to the external data base under that particular type specification, complete information on specific IMD will be presented.

This series of on-line real time steps is repeated for each arbitrary basis triplet identified on the input image. If a sufficiently high number of votes are recorded for entries in the hash table that belong to the same RSFO or IMD, it is considered to be present in the analyzed image, and the code identifying the specific device model is recorded. Although geometric hashing algorithms have initially proven most effective, different algorithms (mentioned above) are also suitable for reliability and further optimization of the interface with the internal STL database itself or some other paradigm of multiple objects features data base.

In some embodiments, the system may include databases populated with substantially all IMDs and potential RSFOs on the market and/or approved by the FDA. After IMD recognition software 430 recognizes the IMD, it contacts IMD database 440 where comprehensive information on the identified IMD is accessed. IMD database 440 is populated with information collected from IMDs manufacturers' specifications, FDA databases containing public health notifications, device safety alerts and recalls, and published peer-reviewed studies. More precisely, information provided includes device model identifiers, all manufacturers' information, including web sites and contact details, general and clinically relevant information, photographs of the device, orthographic plans of the device, examples of the device on different imaging modalities, common issues with the device, potential warnings or FDA recalls and guidelines regarding compatibility with common treatment and diagnostic procedures. IMD database 440 may be modular, expandable, redundant and continually updated. Numerous additions to IMD database 440 are contemplated on a continuous basis; both in terms of newly approved devices, and new updates for already existing FDA approved IMDs. Interactive software components are contemplated in order to eventually enable the system to become part of and facilitate post-market surveillance of IMDs.

Another alternative/possible embodiment is use of pattern recognition and rejection algorithms. This approach starts with methods of algorithm selection based on image pre-processing and pattern recognition using geometric algorithms including line detection, extraction of curve lines, and semantic retrieval by spatial relationships, and structural object resulting in recognition algorithm using shape-form shading. Combination of point, line, peak and curve results in object recognition which is commonly used technique in the computer vision applications. To implement an efficient pattern recognition technique or algorithm, the opposite pattern rejection algorithm must also be designed most specially for applications whenever numerous pattern recognitions are performed. Such pattern rejection must be able to define specific criteria about which pattern must be discriminated from among large classes of patterns. Therefore, rather than creating the axonometric projections database of 3D models of IMDs and/or RSFOs, multiple X-ray, CT, MRI, or ultrasound images of the objects may be used to create pattern recognition algorithm that analyzes geometric and structural patterns from a given image and produce pattern recognition and rejection algorithms that produce the best result when looking for a specific pattern.

One embodiment contemplated is primarily based on geometric hashing algorithms, but this disclosure is not intended to be limited to hashing algorithms. Some embodiments are based on normalized cross-correlation methods/algorithms.

PACSs or modern portable X-ray machines software environments contain an API, which enables them to interface with other software systems. PACS APIs allow communication and data transfer between PACS internal data and functions and third-party programs. In most of the PACS this is accomplished through the introduction of third-party "toolboxes," which is a suitable approach for embodiments of IMD recognition software 430. Upon activating IMD and/or RSFO recognition software 430 through a toolbar available in the PACS's drop tool menu, a raw radiographic image sent from PACS to a separate core software application written in C++ (but not limited to this language) that analyzes the image using pattern recognition algorithms by comparing the 2D representation of an IMD or RSFO to data stored in an system database of their known 3D models or extracted features. The exact model of the IMD present on the radiologic image has been identified using the algorithms described previously, it is cross-referenced with IMD database 440 (which in the exemplary embodiment is RDBMS based) containing further clinically relevant information about the device, which may then be returned to the PACS through its API and provided to the clinician. In the case of RSFO detection—the software may indicate the position of the object by placing an arrow or circle around on the image exported from PACS.

Alternatively, such interaction with the PACS database may be set up through a mobile app, wherein the mobile app user enters the patient information into the app user interface, whereupon the app obtains the relevant image data from the PACS database, activates the RSFO detection and/or IMD recognition software, and once having detected RSFO and/or identified the IMD accesses the IMD database to obtain and display relevant information about the device to the clinician over the app interface. Similarly, this functionality may be incorporated into other systems, such as patient entry systems and patient workflow systems, to provide attending clinicians with relevant data regarding the IMD or the fact that RSFO may be present within the subject patient.

Integration of the core pattern recognition software into standard PACS systems, in the exemplary embodiment, is accomplished through the specific PACS API. Programming of an efficient user friendly interface and integration of specific tools under the PACS environment initially is tailored to the PACS but will be constructed so that it can be easily ported over to other PACS implementations. In some embodiments, the core pattern recognition software module may be integrated into the PACS environment as a utility/dropdown tool menu. After activating RSFO detection/IMD recognition software 430 through the tool bar menu, the software automatically analyses the image or the user circles the noted IMD on the radiological image with a stylus, computer mouse or other input device. When the device has been detected, localized, and identified, additional information about the specific model will be retrieved from the external database and a report in a user-friendly format is sent back to the clinician through the PACS API with an option to automatically include a summary of the IMD information in their radiological report. FIG. 3 shows one of the possible schematic diagrams of the proposed pattern recognition software system.

All software and databases are typically evaluated for functionality, error-tolerance, robustness, connectivity issues, etc. Information provided and recommendations given are intended to be employed as an advisory rather than a definitive diagnostic/identification tool. Furthermore, in the cases where the manufacturer uses the same external casing for different devices (e.g., implantable cardioverter defibrillator and simple demand pacemaker), the software alerts the user and identifies both devices, with corresponding information regarding each IMD.

A goal of the software testing phase is to achieve reasonably high sensitivity and specificity of the core pattern recognition software on simple TIFF images (or any other given format) of XRs, CT, MRI, or ultrasound images of IMDs or potential RSFOs by exploring and optimizing different proposed algorithms. To accomplish this, the algorithms are evaluated using radiographic images of patients with IMDs, which may be obtained from an electronic medical record system. More precisely, images in electronic medical records are mined to identify subjects with IMDs or RSFOs. These are then selected if they have any radiological XR or CT image showing an IMD or RSFO in the PACS. In this exemplary embodiment, these patients then have their diagnostic image downloaded to the research database (for example, a local non-networked database) as a file in the TIFF format. Any information pertaining to the IMD or RSFO (type, manufacture, dates of operation, etc.) is then imported into the database and linked to the corresponding images. This database may thus be cleared of any personal health information. The radiological images are subjected to the previously optimized core pattern recognition software algorithms, after which the accuracy of the detected RSFO and/or identified—predicted IMD is evaluated against the actually implanted IMD, as recorded in the medical records. After optimal methods are constructed, validity and reliability will be reevaluated, including testing the algorithms against new sets of images. Algorithms and model performance are selected and adjusted to achieve optimal identification/discrimination. The associated indices of precision, specificity, sensitivity, accuracy are evaluated and provided so that the exemplary embodiment has a persistent ability to continuously refine and improve its recognition efficiency. In one embodiment, the software is subject to regulatory approval, for example, being submitted to FDA approval for clinical practice (after rigorous and robust testing).

Examples IMDs:

The following examples show how embodiments of the system and methods of the invention have been or could be used in clinical situations. These examples include hypothetical elements showing how the system could be used.

First, consider an example involving an emergency situation where the recognition of an implanted medical device is important to the proper treatment of the patient. A 68 year-old male involved in a high-speed automobile accident, is brought to the emergency department. Chest and abdomen XRs and trauma CT scan show multiple fractures, air and bleeding in the abdomen, and possible traumatic brain injury. The surgical team requests an immediate emergent exploratory laparotomy, and anesthesiology is consulted. Both radiologist and anesthesiologist notice on the chest XR and CT images of an unknown implanted medical device (IMD) in the left upper quadrant of the chest. The lead surgeon and the anesthesiologist consult regarding whether the patient is ready for surgery. The surgeon indicates that "the patient has an IMD but since there are no medical records available for this patient and the patient's wife is in no condition to answer questions, and we don't know what type of device. We need to know the type of device and whether the patient is device dependable. In addition, we should know whether the device should be turned off as it would possibly interfere with the electrical cautery during surgery. I also need to evaluate whether this patient has a spinal cord injury. Can we at least get an MRI on this patient?" The anesthesiologist replies "Well we do not know whether the device is compatible with MRI yet," and uses the system to identify the IMD from the recorded images on the PACS system. In one embodiment, the anesthesiologist selects "IMD Identification" from a drop-down tool in the toolbar menu bar of the PACS environment, giving access to the IMD identification pop-up tool bar, hitting the detect button. The IMD identification software selects all possible IMD's on the image, in this case just one. The anesthesiologist selects the IMD portion of the image on the screen and then clicks the identify button. Within the IMD identification software, after segmentation and selection of the radiographic image of the IMD, that portion of the image is analyzed by the core object/pattern recognition software. Prior to feature extraction, imaging artifacts are removed and/or adjusted while contrast and other image attributes are optimized using appropriate algorithms. By using edge and corner detection algorithms unique feature points are identified in the input image and feature points (non-collinear triplet) are arbitrarily selected in the input image. Furthermore, affine coordinates of the remaining feature points identified in the input image are calculated, and for each such coordinate, the entire hash table contained in the internal stereo lithographic database is searched for an appropriate match. This series of steps is repeated for each arbitrary basis triplet identified on the input image. If a sufficiently high number of votes are recorded for entries in the hash table that belong to the same IMD, it will be considered to be present in the analyzed image and identified. Once this criterion has been achieved a pop-up window with the name of the device is displayed. Along with the identification, another button labeled additional information is displayed which links to a data base containing extensive information about the device in a user friendly manner (given the potentially huge size of this IMD detailed information database, in most embodiments this database will be externally stored and accessed remotely). This information may be displayed in a separate window after the click on the additional information. Therefore, the IMD identification software tool may be located on the quick access toolbar under a PACS environment and provide the physician with needed information in an efficient and timely manner.

In the hypothetical example started above, after the anesthesiologist selects the identify button, another window pops up identifying the type of device as a pacemaker and the manufacture and model of the device: XYZ manufactured by XZY. In addition, information regarding the clinical management of the device is shown in a user friendly manner after an additional click, including MRI compatibility, electrocautery interference, type and make of external programmer etc. In this example, the IMD needs to be turned off during surgery. The additional information button activation results in a new window which comes up on the screen. With an overview of the detailed information, the anesthesiologist determines that an MRI may be taken but that during surgery that particular IMD must turned it off, and the additional information indicates that it may be turned off by placing a magnet above the battery and generator during the surgery. In addition, external pacing should be provided during the surgery. The additional information displayed in the window also notes that the particular pacemaker should be reprogrammed after the MRI, so that the clinical staff is alerted to call for cardiology consult and inform them with the type of pacemaker. The patient was subsequently taken for the emergency surgery in a safe manner. The provided information also indicates that the device is compatible with the MRI imaging. Furthermore, the device identification helped cardiology team to use appropriate device specific external programmer to reprogram device in the postoperative period in the intensive care unit ("ICU"). Therefore, the rapid identification of IMD was crucial for the emergent management of the patient.

In a second example, the system may also be used to recognize and help assess IMD in non-emergency situations.

Consider an example involving a 46 year-old patient admitted to an emergency department due to increased spasticity. Her daughter indicates that she had a past medical history of spinal cord injury/transection and had a programmable drug infusion system implanted in her abdominal wall due to her chronic pain and spasticity. As she does not have any documentation regarding the implanted medical device and cannot remember the model or specifics of the device, the first step is to check the structural integrity (possible tubing disconnection) and try to determine the type of the implanted programmable infusion pump. In order to do so, a recent XR of the abdomen is analyzed. Upon visualization of the device on the XR or CT images the physician uses the drop-down tool menu in the PACS environment. After identification of the device type detailed additional information on this specific device was provided. This prompted check-up of the device by the appropriate specific external programmer indicates that the pump uses baclofen. It also indicates low level of baclofen in the pump reservoir. This prompts a transcutaneous injection of the baclofen into the pump reservoir, pump reprogramming, and subsequent patient improvement. All these steps have been described in detail, in the separate window that pops up after an additional click on the name of the device in the initial window that popped up and displayed the basic name and type of the device.

A third example shows the usefulness of the system in implementing IMD recalls. In this hypothetical situation, a 75 year-old patient is admitted for elective inguinal hernia surgery. After taking a chest XR, the attending physician notices an IMD on the image. The physician pulls up the image of the XR on the PACS system and selects "IMD ID" from a drop-down tool in the menu bar of the PACS environment. In this example, this menu provides access to an IMD identification pop-up tool bar. The physician selects the detect button activating the IMD identification software to select possible IMD's on the x-ray, in this case just one and clicks the identify button. In response, the system provides a pop-up window designating the name and type of device: Like a prior example, the further IMD information shows that the device may be turned off by placing a magnet above the battery and generator. Additionally, a further information window also includes a flashing "Warning Recall!" message that includes specific information on the recall of this specific device. In this example, the pacemaker model was recalled by the manufacturer just a few days prior to the patient visit because of battery shorting problems with this particular device. This allows the physician to plan to replace the battery and generator in tandem with the inguinal surgery. Once it is determined that it was a defibrillator not resistant to electrocautery interference, the decision was made to turn it off during surgery by placing a magnet above the defibrillator battery and generator casing. The patient is subsequently taken for the surgery in a safe manner. However, although the pacemaker was functioning properly, the database indicated a red flag to the physician that the identified pacemaker model was recalled by the company just a few days before his admission and prompted replacement of the battery and generator by the cardiology team during the same anesthesia for the inguinal surgery. Therefore, this enables the physicians to do both surgeries under the same anesthesia and avoid the risk of additional anesthesia and surgery for the patient in addition to the benefit of timely replacement of the device.

Figure 5:
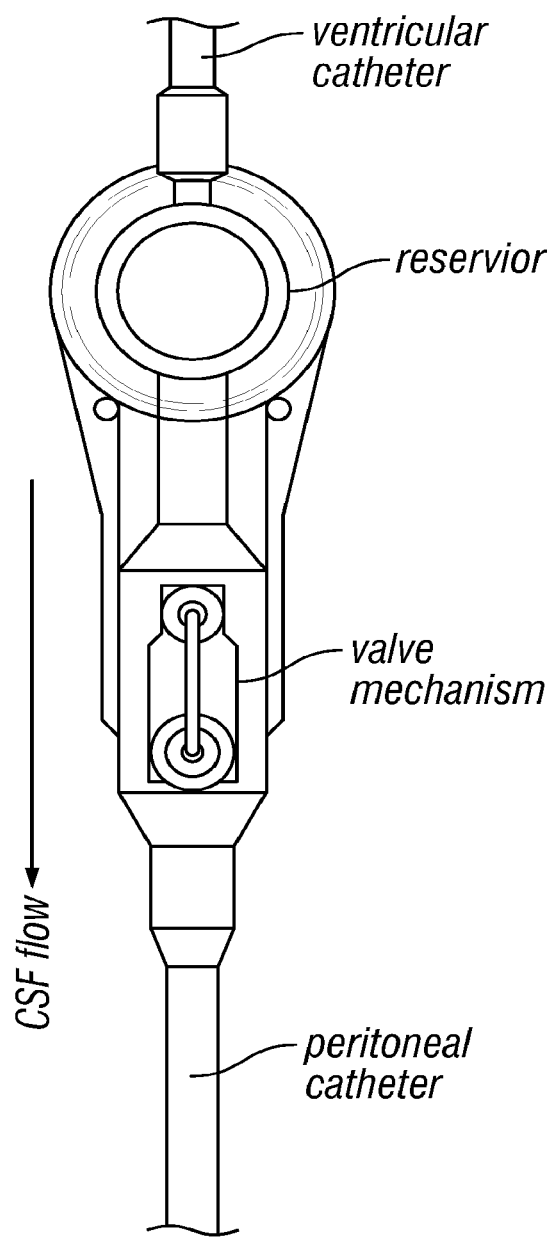
FIG. 5 is a top plan view in partial cross section showing a particular IMD in reference to its connections with tissue.

A fourth example involves the recognition and assessment of the structural integrity of the IMD. In this hypothetical example, a 12 year-old patient with past medical history of hydrocephalus is admitted to the emergency room for increasing headaches. The patient's mother reported that the patient has a ventriculo-peritoneal shunt and that he had multiple surgical shunt revisions in the past. The mother does not know the exact type of the most recently implanted shunt valve. More precisely, when extra pressure builds up in the brain ventricules, the valve opens, and excess fluid drains out of it into the abdominal cavity. This decreases intracranial pressure. The valves in newer shunts may be programmed to drain more or less fluid from the brain. Upon neurosurgical evaluation the shunt XR series is ordered. To provide proper treatment, the physician needs to know: (1) The type of the valve; (2) Whether the valve is compatible with MRI imaging; and (3) Whether the structural integrity of the device was preserved. Upon visualization of the shunt valve on the XR images, the physician may use the drop tool menu in the PACS environment, and click identify button. After the device has been recognized, the physician may also click on the "structural integrity check" button under the same drop tool menu. The structural integrity procedure checks that the device falls within normal parameters and if there are deviations from the norm for that device, and the possible reasons for the deviation (i.e. disconnection or crack). It indicates where the deviation occurs, the models (computer generated overlay of device) of the correct IMD and a quantitative measure of the amount of deviation (a percentage value or bar). The IMD identification software determines the type of the shunt valve and that valve is compatible with MRI imaging—but requires reprogramming afterwards. In addition, the IMD identification software indicates that there is a gap between the valve and radiopaque tubing on the proximal side which indicates disconnection. More precisely, shunt valve (see FIG. 5) is plastic and radiolucent. The only part of the valve visible on the x-ray is a small metal valve mechanism; the rest of the device is relatively invisible on the image. On the other hand, the tubing connected to the valve is radiopaque. Therefore, without the IMD identification software, unless the radiologist knows the exact dimensions of the valve, it is practically impossible to diagnose close disconnection of the peritoneal/distal or the ventricular/proximal catheter from the shunt valve. This is further complicated if the X ray image was taken under the angle. However, disconnection is one of the most common reasons for shunt malfunction. In this case, the IMD identification software indicates that a gap between the metal-part/valve-mechanism and tubing is not consistent with a computer model of the known dimensions of the valve and the locations of the connecting areas thus indicating possible disconnection. Upon closer examination of the images, radiologist confirms IMD identification software (acting as an advisory tool) finding, and issues a report that prompts valve revision and/or replacement by the neurosurgery team. Therefore, the rapid identification of IMD is crucial for the safe emergent management of this patient. In addition, usage of this software is envisioned to contribute to the reduction of the incidence of shunts disconnection misreads which is very common mistake in radiological practice. Therefore, considering that the most common reasons for the malfunction of IMDs are disconnections and cracks of its elements and/or connecting wires—which are also difficult to diagnose from radiological images, the same concepts/pattern recognition software can be used for the assessment of the structural integrity of the IMDs. Pattern recognition software creates a computer model of the IMD components in the analyzed location and check to see if the location of the IMD is compatible with the locations of the other radiopaque elements such as wires/ leads/tubing to which the IMD is expected to be connected/attached. More precisely, upon identification of the IMD itself, the IMD recognition software analyzes images in the assigned radiological study for any disconnections and/or cracks of IMD's elements and automatically notifies the clinician if any of those are possibly detected.

A fifth example involves recognition of an IMD to prevent adverse procedures. In this hypothetical example, a 73 year-old patient is admitted to hospital and treated due to liver decompensation/failure. He has a pacemaker and currently has no cardiac issues. After the new team of residents is assigned to the patient, a new intern notices a significant cardiac history and the fact that the patient has a pacemaker. As the medical records were unclear as the device was exchanged and updated several times, the intern wants to add correct current information to patient medical records. So the intern checks the most recent chest X-ray image. Upon visualization of the pacemaker on the XR image he uses a drop tool menu in the PACS environment, encircles the device, and clicks the "identify" button. Upon identifying the pacemaker, he updates the institutional patient medical record with the type of the device and also checks whether the device is compatible with MRI imaging which is scheduled for the following day. Upon seeing from the pop-up window that the pacemaker is not compatible with MRI imaging, alternative procedures are scheduled. This prevents a serious/potentially fatal mistake in patient management.

A sixth example involves providing clinical feedback to IMD manufacturers. In this hypothetical example, incidents of improper structural integrity are noted in the system database. Where structural integrity issues have been repeatedly detected with the same specific implanted medical device in different patients, the database portion of the IMD recognition software updates and/or corresponds this information to the manufacturer. In this specific example, the cardiac leads disconnections from the battery and pulse generator are identified multiple times (multiple patients) in the same device starting approximately two years after it arrived on the market. Such disconnection was noticed in XY patients over the period of X months. This information prompts a statistical trigger and careful review of these cases. Subsequently the manufacturer decides to recall this particular device in a timely manner.

Figure 7A:
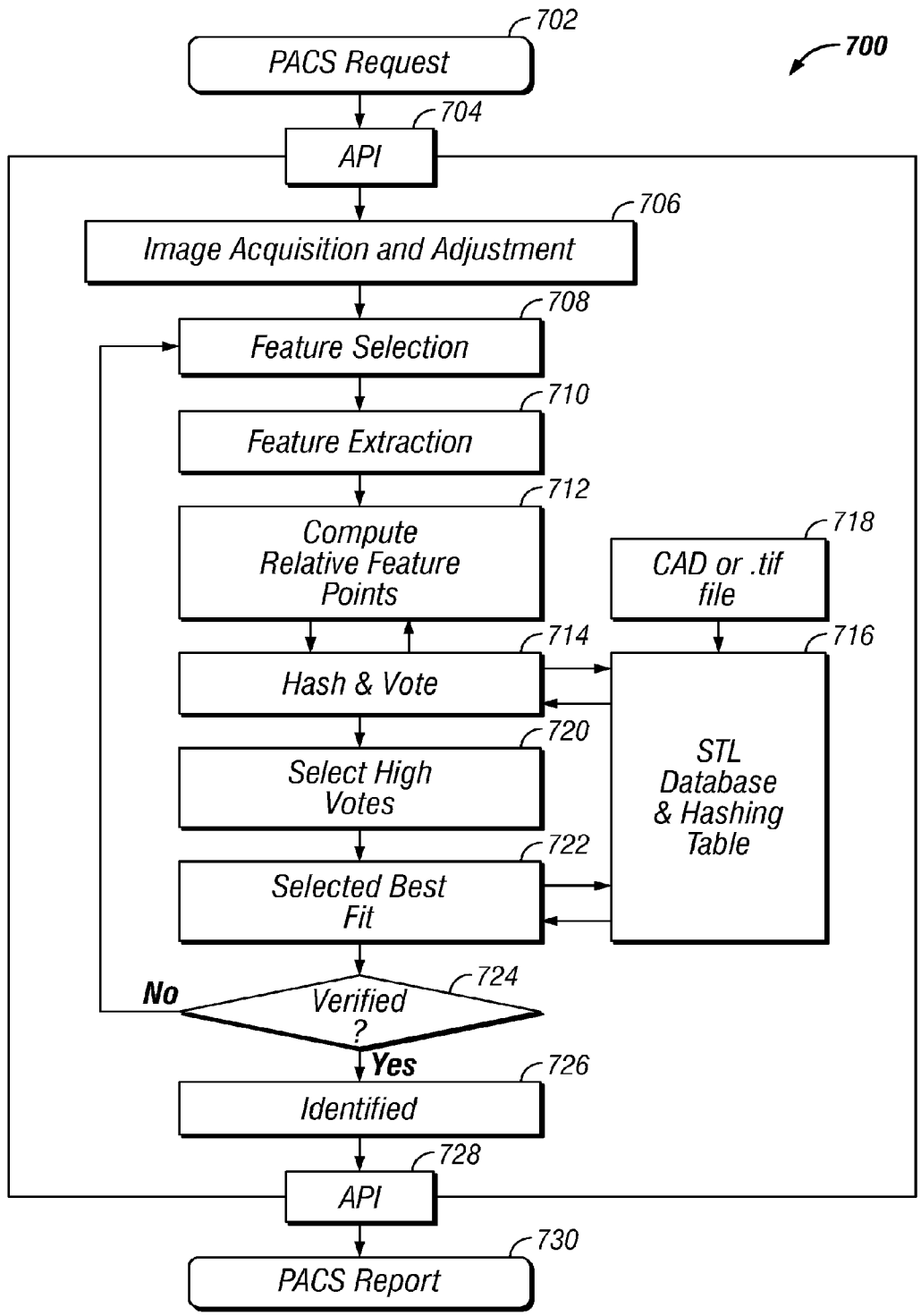
FIGS. 7A-7D show flow chart diagrams relating to the operation and use of an embodiment of the present disclosure for identifying RSFOs.

RSFO Identification:

FIGS. 7A-10B show an embodiment for detection and identification of RSFOs. FIG. 7A shows flow chart 700 of one embodiment wherein pattern recognition software is called by a PACS. As described in greater detail below, PACS request 702 is routed to API 704 so that pattern recognition software may begin its execution with image acquisition and adjustment step 706, in which one or more digital images are received from the PACS and optionally adjusted for contrast. The adjusted image then is evaluated for features in feature selection step 708, and when found features are extracted in step 710. In step 712 the relative positions of the feature points are calculated then run through the hash algorithm in step 714, where potential matches in the STL database are evaluated in step 716 in conjunction with a hashing table and images from known objects in step 718. Although this example uses geometric hashing algorithm, embodiments are contemplated in which numerous algorithms could be used to identify a RSFO. In some cases, for example, multiple recognition algorithms could be used to determine the RSFO. A non-exhaustive list of algorithms that may be used to identify a RSFO is discussed above. Based on the computations of steps 716, and 718, step 714 counts the votes for each feature and selects those having the highest number of votes in step 720, with the selected features being evaluated for the best fit in step 722 (again in combination with the STL database, hashing table, and object images in the processing of steps 716 and 718) then tested for verification in step 724. If verified, the selected best fit of the selected features are identified in step 726, those results returned via API 728 to PACS for report step 730.

Figure 7B:
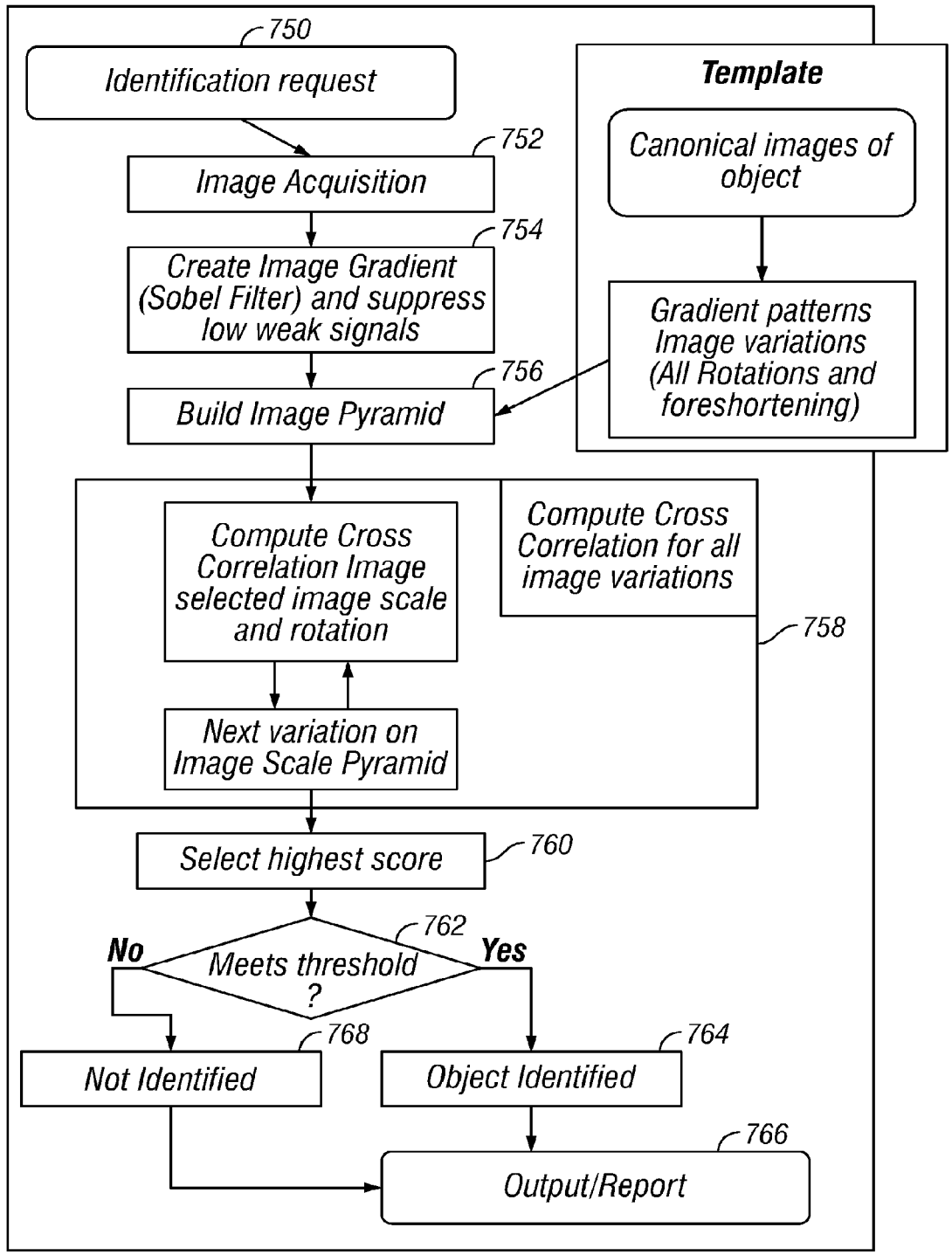

FIG. 7B shows a flow chart of an embodiment of a detection algorithm for detecting/identifying RSFOs and/or IMDs, particularly a needle. In the example shown, a request for identification of a RSFO and/or IMD is received in step 750. For example, the request may be initiated by a mobile device communicating with PACS or by a selection from the interface of the PACS. The medical image is acquired (step 752) and image gradient is created (such as using the Sobel filter) and low weak signals in the image are suppressed (step 754). A pyramid representation is built based on canonical images of the object (e.g., a needle) in isolation, which are then rotated and foreshortened across a range of angles/factors (step 756). The cross correlation for all image variations is computed (step 758). The top scoring object based on this analysis is selected (step 760). If this score meets a threshold value (step 762), the object with the highest score is identified (step 764) possibly in a report (766). If the score does not meet the threshold value (step 762), the object is not identified (step 768), possible in a report (step 766).

Figure 7C:
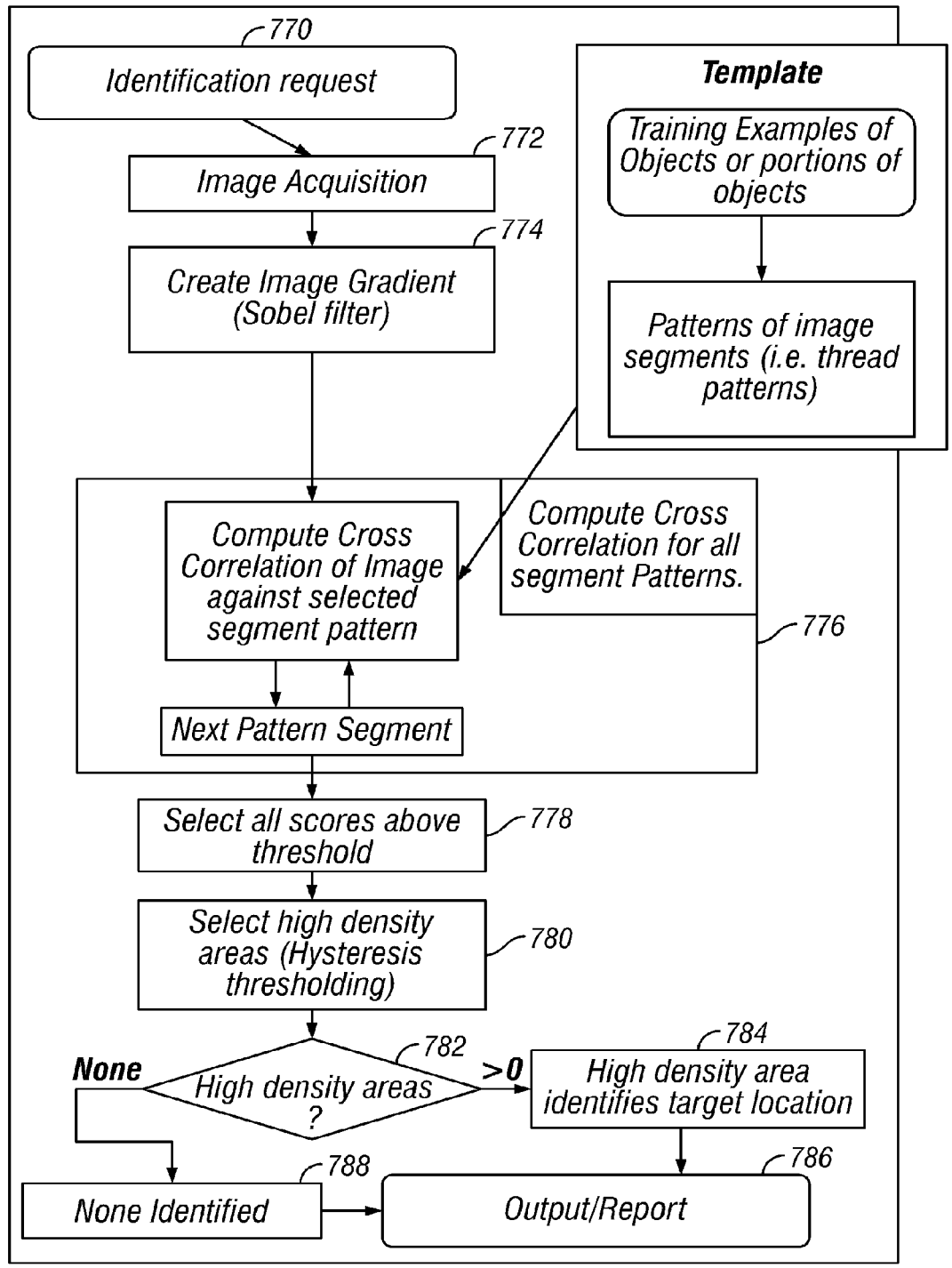

FIG. 7C shows a flow chart of an embodiment of a detection algorithm for identifying RSFOs and/or IMDs, particularly a sponge. In the example shown, a request for identification of a RSFO and/or IMD is received in step 770. For example, the request may be initiated by a mobile device communicating with PACS or by a selection from the interface of the PACS. The medical image is acquired (step 772) and a image gradient is created, such as using the Sobel filter (step 774). The cross correlation for all segment patterns is computed (step 776). In this example, this is computed based on training examples of object or portions of objects and patterns of image segments. All scores that were computed above a threshold are selected (step 778). Of these, the high density areas are selected (step 780). A determination is then made whether these include any high density areas (step 782). The high density areas are identified as target location(s) (step 784) in a report (step 786). If no high density areas are found, no objects are identified (step 788) in the report (step 786).

Figure 7D:
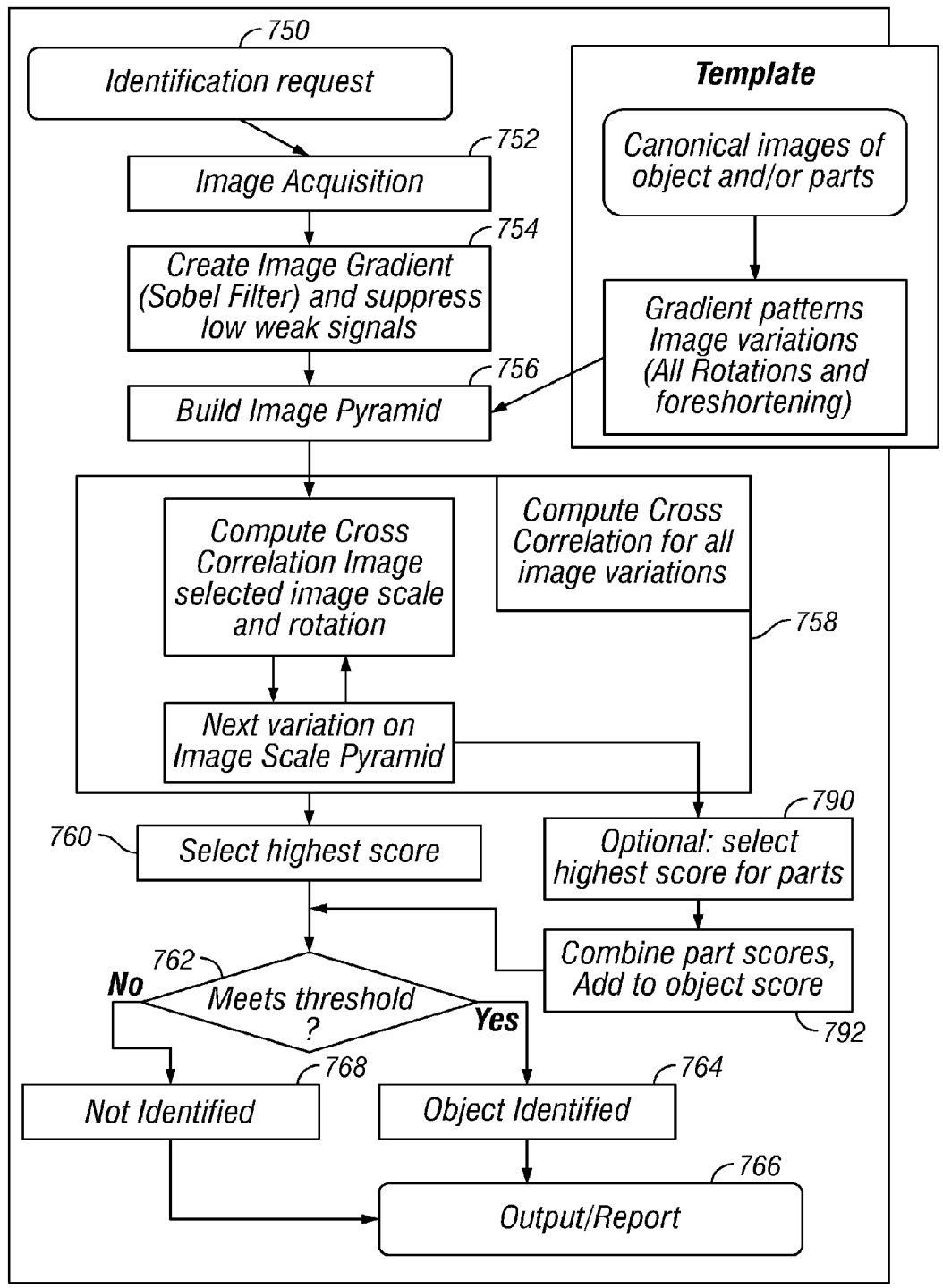

FIG. 7D shows a flow chart of an embodiment of a detection algorithm for identifying RSFOs and/or IMDs. This example is similar to the approach shown in FIG. 7B, except that this example includes options steps of selecting a highest score for parts (step 790) and combining the part scores and adding with the object score (step 792).

There are no specific configurations needed of PACS required to achieve the procedure referred to in FIGS. 7A-7C. Embodiments of the pattern recognition software may be integrated in both PACS systems and different software interfaces of portable X-ray machines through APIs of such X-ray machines. Therefore, some embodiments may provide instantaneous information after the X-rays are obtained by portable X-ray machines in the operating room. In addition, once images are uploaded in the PACS, other embodiments may be integrated as a drop down tool menu of a PACS so that the physician uses the pattern recognition software to check X-ray of pilot CT images for any RSFO.

In addition, other embodiments may include automatically analyzing routine post-operative day CT scans and X-rays on postoperative days 1 and 2 for any possible RSFO (e.g., to guard against the occasion where although the counting was performed it was not accurate).

In terms of the STL or specific features data bases of all IMDs, surgical instruments, radio opaque markers of the sponges, implanted prosthetics and surgical devices, and needles there is no need for any specific implementation. 3D models of the all possible RFSOs will be generated by using all the available technologies including AUTO CAD files obtained directly from the manufacturer, 3D scanning, series of device X-rays, 3D reconstruction from the plans etc. An internal data base may use STL format of these images but not limited for this particular algorithm which is part of geometrical hashing. This data base may possible contain other formats and extracted features of the IMDs, surgical instruments, radio opaque markers of the sponges, implanted prosthetics and surgical devices, and needles that will enable their identification from the 2D images. Again this depends on what algorithm will be optimized for identification of specific possible RSFO.

Figure 8A:
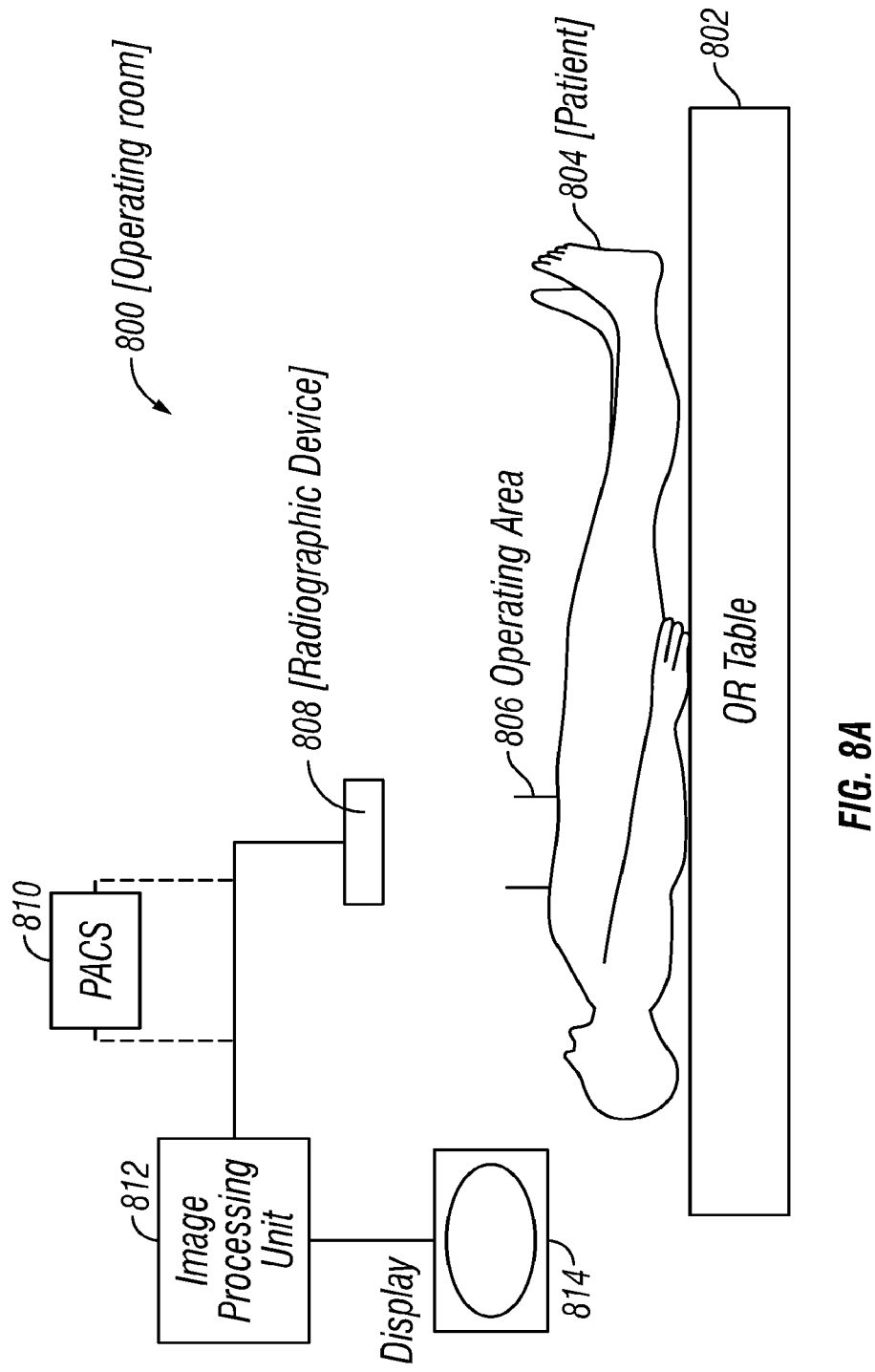
FIG. 8A is a schematic diagram of an embodiment of an operating room system of the present disclosure identifying RSFOs.
Figure 8B:
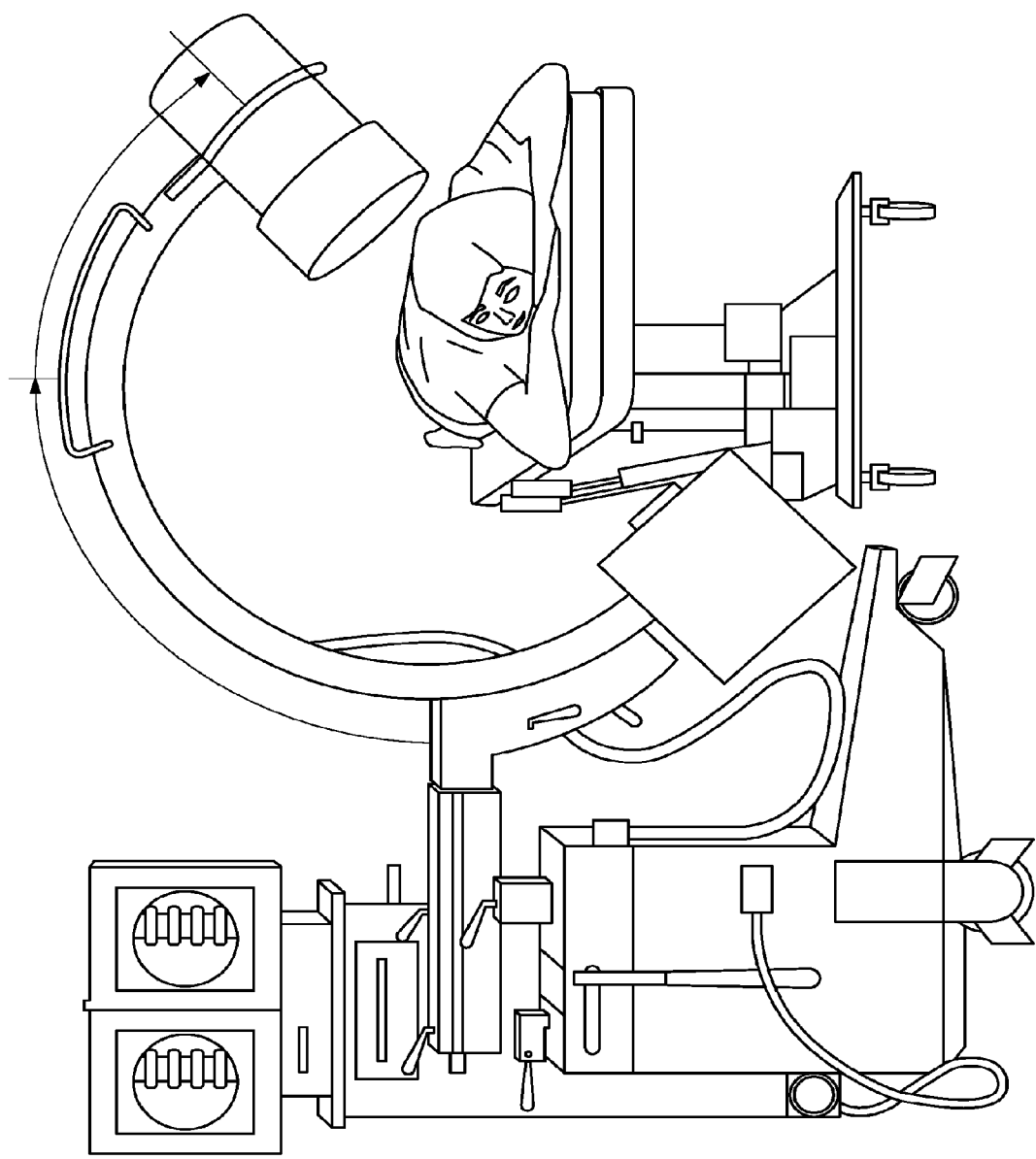
FIG. 8B is an exemplary diagram of a system shown in FIG. 8A.

FIGS. 8A and 8B show one embodiment of a system as deployed in operating room 800. Operating room table 802 supports patient 804 during surgery on surgical operating area 806. Radiographic device 808, for example an x-ray, CT, or magnetic resonance imaging (MRI) machine is positioned proximate operating area 806. During a surgical procedure, radiographic/diagnostic device 808 may send images, optionally via PACS 810, to image processing unit 812, for example a personal computer or tablet. Optionally, display 814 may be disposed within operating room 800 so that the results of the RSFO detection or IMD detection and identification software of unit 812 may identify them apparent on images from radiographic device 808 so that the surgical staff may take appropriate actions.

In other embodiments, the pattern recognition software is installed/integrated into software interfaces of conventional portable X-ray machines such as shown in FIG. 8B. Most conventional portable X-ray machines have 360° C. arm (or similar solution), integrated screens, integrated computer with processing power, and software interface. Having integrated software within the portable X-ray machine enables accurate targeting and high quality images and employs anatomical programs that not only set the imaging conditions, but also handle such tedious tasks as adjusting the image orientation as well as other parameters. Image memory and other functions offer powerful operator support. Therefore, once the operator takes the X-ray image, one of the available tools/options in such embodiments involves analyzing the image for any of the potential RSFOs or IMD detection and identification. If the portable X-ray machine does not have sufficient image processing capabilities, then the obtained X-ray image may be analyzed once exported to PACS. Similarly, portable CT scan machines may be provided with integrated pattern recognition software.

Software for the detection of RSFOs or IMDs from the X-ray images is based on pattern recognition algorithms. Software modules for graphical input analysis, feature selection and extraction, pattern recognition based on two dimensional (2D) axonometric projections of the three dimensional (3D) models of RSFO, and decision making based on feature matching, statistical, and syntactic approaches are included. Specific algorithms best suited for the RSFO recognition from multiple 2D radiographic images are used. These algorithms are further combined with probabilistic ranking, perceptual organization, and spatial correspondence algorithms for recognition from single 2D radiographic image. Such recognition is made possible by generating a plurality of projections for each possible object, so that the three dimensional object does not need to be identified—only one of the representative two dimensional projections need be identified.

Thus, databases of 3D models or specific extracted object features of potential RSFOs including surgical instruments, needles, and radio-opaque markers of sponges, gauze towels, and laparotomy pads is the starting point. Using these 3D models, a database of their axonometric projections is generated for a plurality of axiomatic orientations. Existing computer assisted design (CAD) files (for example, provided by manufacturer or Food and Drug Administration) may be used to create the database, or alternatively new data base files may be created using a 3D scanner. Specific feature data base may be created based on analysis of multiple diagnostic images of the IMD or potential RSFO. These axonometric projections are used by the software for RSFO comparison/detection in X-rays and other kinds of diagnostic images.

Pattern recognition algorithms may be created based on graphical input analysis and RSFO feature selection/extraction relaying on their comparison with the axonometric projections data base. Thus, for a particular set of objects, an optimized pattern recognition algorithm may be employed. Alternatively, a database of a universal set of objects may be created, and a more generalized pattern recognition algorithm may be used. For the purpose of having a fast algorithm that may identify potential RSFO's while a surgery is still in progress, it may be advantageous to start with a limited set of objects and an optimized pattern recognition algorithm. In one exemplary embodiment, such an optimized pattern recognition algorithm was developed to have as criteria for acceptance: Achieving >95 sensitivity and specificity for the plain orthogonal (rotation only in z-axes) X-ray images of the 10 scanned objects and subsequently for any given projection angle (rotation in all three axes). Once optimal algorithms are created, sensitivity and specificity may be further evaluated by testing the optimal pattern recognition algorithms on X-ray images of multiple known images with some of the set of objects.

In other embodiments, the 3D model/axonometric projections database may be expanded to include all commonly used surgical tools (small size instruments in standard OR sets), needles, and surgical materials' radio-opaque markers. The pattern recognition algorithms for recognition of these objects may be further refined and evaluated in a similar manner described above.

In one embodiment, the pattern/object recognition and database-access algorithms are implemented in a Visual C++ software environment (Microsoft, Redmond, Wash., USA) and a widely available cross-platform relational database management system is used to host the database (such as MySQL Enterprise, Microsoft SQL Server, or Oracle Database Enterprise).

In another embodiment, the pattern/object recognition software is implemented in MATLAB GUI (MathWorks™, Natick, Mass., USA). In this embodiment, the software is capable of recognizing a common surgical needle in the orthogonal X-rays (needle rotated only around z axes with fixed x and y axes) of the needle itself; i.e., no patient or dummy. [00139] Further concept testing embodiments may be developed using historical image data and object usage data. For a particular surgical location, or even a particular type of surgery, patients may be identified with multiple intra-operative X-ray images and/or history of RSFOs in the particular PACS/digitalized medical record system. These medical records may be mined and subjects with the history of a RSFO or multiple intraoperative X-rays (which still may be used for testing/identification or visible surgical instruments) are selected and their intra operative X-ray images downloaded to a database (which may also be cleared for any personal health information). The pattern recognition algorithms developed for other locations and/or types of surgery may then be tested. Particular algorithms and mode performance may be adjusted to achieve an optimal identification so that achieving overall >95 sensitivity and specificity in real patient images is obtained.

Embodiments of pattern recognition software of the invention may be integrated into PACSs and/or portable X-ray machine software environments as a tool menu, such as an addon program, an additional pull-down menu, or a sub-menu option within the system software. In one embodiment, an API of the PACS or portable X-ray machine software is used to integrate the pattern recognition software. All major PACS and portable X-ray machines software packages/user environments contain an API, which enables them to interface with other software systems. They are able to output data to a third-party program and receive input from other applications. In most of the PACS this is accomplished through the introduction of third-party toolboxes/drop down tool menu(s), which may be implemented in several embodiments of the invention. Upon activating the pattern recognition software through a toolbar available in the PACS or portable X-ray machines software environment, a radiographic image is sent to the pattern recognition software that adjusts and analyzes the image using pattern recognition algorithms—essentially comparing the encountered 2D representation to the 2D axonometric projections database of known 3D models of RSFO or comparing object features to the database of specific previously extracted features from the series of the 2D images of the 3D objects. Ideally, the pattern recognition database would contain axonometric projections of the 3D models of all potential RSFOs including standard surgical instruments, needles, and radio-opaque markers of surgical materials. However, it may be advisable to limit the size of the database because of hardware constraints, in which case knowing the exact list of possible objects may be necessary depending on the circumstances.

The pattern recognition software shortens the analysis time for the detection of RSFO(s) in radiological images. More precisely, pattern recognition software/algorithms are far more efficient in the detection of such objects with the known and constant dimensions then human eye and complete this task instantaneously. Therefore, such software provides more efficient (better, faster, less expensive) detection of RSFOs in comparison with the current protocols. In addition, the image is automatically processed to remove imaging artifacts and adjust the contrast by using specific processing algorithms that maximize the possibility for RSFO detection. These features lead to near instantaneous RSFO detection with both a sensitivity and specificity approaching 99%. Furthermore, this software provides near instantaneous detection of the 3D RSFOs' position/location within the operative field in a series of X-ray images once the RSFO has been identified.

The overall effectiveness of intra-operative radiographs in detection of RSFOs is limited by the sensitivity and specificity of the human eye, quality of communication between the OR team and radiologist, quality of X-ray images, subjectivity of the surgeon or radiologist, and lack of their formal training in recognizing RSFOs. Pattern recognition software/algorithms are far more effective in the detection of the objects with the known and constant dimensions and complete this task nearly instantaneously. Furthermore, the image is processed to remove imaging artifacts and adjust the contrast using appropriate algorithms that will maximize the possibility for the RSFO detection. Therefore, this software/advisory tool greatly increases RSFO identification sensitivity and specificity and shortens the time of x-ray image analysis.

If the RSFO is identified, additional projections/portable X-rays are usually necessary to approximate the position of the RSFO in the surgical field. This is particularly relevant in emergent abdominal or chest surgeries that have relatively large operative fields. Therefore, by rapidly identifying the RFSO(s) in different projections, this software also significantly shortens the time needed to locate the RSFO within the surgical wound/field. In the event of an incorrect count the portable X-ray of the operative field should be made available to the radiologist within 20 minutes while the radiologist evaluation/confirmation to the surgeon in the OR should be completed within another 20 minutes. On average this entire process takes approximately 30-40 minutes. Embodiments of the inventive pattern recognition software significantly shorten this time. This is particularly advantageous if the patient is unstable. Furthermore, this also shortens the anesthesia time and associated risks.

Integration of the pattern recognition software into PACSs and/or portable X-ray machine software environments through their APIs makes this software widely applicable in everyday clinical practice. This pattern recognition software directly translates the novel computational technologies and software algorithms into clinical practice and solves emerging clinical problems in an efficient manner. Pattern recognition software is a rapidly developing field, examples of which range from simple, such as reading bar codes, to extraordinarily difficult, such as voice recognition, automatic recognition of objects, or individual people identification from photographs or live streaming aerial videos. Image analysis is largely based on algorithms for pattern recognition, which refers to detection of meaningful patterns in raw image data.

In some embodiments, detection of RSFOs from X-ray or CT images and/or any other type of diagnostic imaging is based on pattern recognition algorithms. Software modules for graphical input analysis, feature selection and extraction, pattern recognition based on 2D axonometric projections of the 3D models of RSFO, and decision making based on feature matching, statistical, and syntactic approaches are generally included. Specific algorithms best suited for the IMD identification and/or RSFO detection from single 2D radiographic image or from multiple such images are used. In some embodiments, feature extraction methods include edge detection, interest point detection including Harris, Kadir-Brady, Difference of Gaussians, Harris-Laplace, Maximally Stable Extremal Region detectors, and other interest point detection methods. Methods for recognition of objects based on known 3D models include, among others, parametric and generalized Hough transforms, geometric hashing, implicit shape models and other voting-based methods. Recognition by parts includes, among others and in addition to variants of methods mentioned above, constellation models, poselets, pictorial structure methods, 2D and 3D deformable parts models, grammar and topic models. Appearance-based methods include, among others, template matching, edge matching with Chamfer and distance transforms, active contours, medial axis matching, gradient matching, and correlation based matching. Feature representations used in any of the above methods may include, among others, shape contexts, scale-invariant feature transform, speeded up robust features, histograms of oriented gradients, local binary patterns. Embodiments are contemplated in which detection and/or identification is primarily based on edge detection, gradient matching, normalized cross-correlation and kernel density estimation, but not limited to these particular algorithms/methods as we may use other above mentioned algorithms/methods. All the above mentioned algorithms may alternatively be used in certain situations. These algorithms are further combined with probabilistic ranking and hypothesis testing, perceptual organization, and spatial correspondence algorithms for recognition from single 2D radiographic image. Such recognition is made possible by generating a plurality of projections for each possible object, so that the three dimensional object does not need to be identified—only one of the representative two dimensional projections need be identified. Current and here submitted software prototypes—embodiments of invention—are based on normalized cross-correlation methods/algorithms.

Again, the mathematical methods and algorithms used in image analysis and pattern/object recognition are well described and broadly available. Recognition of objects based on known CAD 3D models includes edge detection, primal sketch, Marr, Mohan and Nevatia, Lowe, and Faugeras methods. Recognition by parts includes Binford, Biederman, Dickinson, Forsyth and Ponce methods. Appearance-based methods include edge matching, divide-and-conquer search, grayscale matching, gradient matching, and large model bases systems. Feature-based methods include interpretation trees, hypothesize and test, pose consistency, pose clustering, invariance, geometric hashing, scale-invariant feature transform, speeded up robust features. Other complex approaches include template matching, gradient histograms, intraclass transfer learning, explicit and implicit 3D object models, global scene representations, basic and complex discrimination, shading, reflectance, texture, grammars, topic models, window-based detection, 3D cues, context, leveraging internet data, unsupervised learning, and fast indexing. Embodiments of the invention may be primarily based on geometrical hashing but not limited to this particular approach as the other above mentioned algorithms may alternatively be used in certain situations.

RSFOs are essentially three dimensional physical objects unintentionally retained in patients' bodies. Broadly, they are usually made of biocompatible metal alloys such as surgical instruments or different surgical fabric materials such as sponges, gauze towels, and laparotomy pads that contain radiopaque markers. Examples of radiographs of a flat and crumpled sponge with radiopaque markers are shown in FIGS. 9A and 9B, wherein the radiograph markers of the exemplary sponges have a double helix shape. With the sponge radiographs, the definable points are the intersection points of the radiograph markers. In addition, the radiographic lines of the markers have a known thickness, so that the orientation of the sponge relative to the radiograph may be in part determined by the thickness of the marker line on the radiograph. A 3D model of the sponge may also be generated based on the variation of marker line thickness. Such a 3D model may not necessarily precisely locate the entire sponge, because portions of each sponge do not contain radiographic markers. However, having a known position and orientation of a sponge's radiographic marker provides an approximate zone where the remaining portions of the sponge are likely to be located.

Examples of needle radiographs are found in FIGS. 10A-10C, wherein a generally arc shaped needle may appear straight, slightly bent, or as a true arc depending on the plan view. In addition to radiographic projections, in some embodiments models of the structure of each potential needle are included in the pattern recognition. In these embodiments, the structural integrity of the needle may be evaluated against the radiographic image. This allows for the display to indicate not only the position of a needle in the surgical site but additionally may indicate if the needle is partially bent or broken—important information for the retrieval of the needle. A bent needle may need to be removed in a non-standard procedure, and a broken needle may indicate that the surrounding tissue should be inspected for possible needle fragments. In some embodiments of the invention, the pattern recognition software generates projections of the missing portion(s) of a needle and searches the radiograph for the corresponding piece(s).

Because the density of these materials, e.g. needles, sponges, etc., is generally different than that of tissue, RSFOs are visible on X-ray images. Data obtained in virtually all medical imaging modalities typically includes 2D representations of 3D structures, making the radiographic images obtained effectively a type of axonometric projection. It is worth noting that this is true even in certain 3D medical imaging modalities where sophisticated 3D reconstruction processing takes place after a series of multiple 2D images has been obtained. Geometrically, 2D axonometric projections are affine transformations (involving rotation, scaling and shear) and translations (shifts) of combined orthographic projections ("plan views," a collection of which makes up a complete 3D model of an object). This makes it mathematically possible to analyze a single 2D radiographic image of an RSFO and, if a 3D model of that particular object is known and available, match it to a particular model.

In one embodiment, the pattern/object recognition and database-access algorithms are written in Visual C++ (Microsoft, Redmond, Wash., USA) and a widely available via a cross-platform relational database management system (RDBMS) (such as MySQL Enterprise, Microsoft SQL Server, or Oracle Database Enterprise).

Again, pattern recognition software development and optimization may be programmed using Visual C++ or a plurality of other computer languages. As previously explained, 2D contours of RSFOs on radiographic images are analyzed as axonometric projections of 3D models of the surgical instruments, needles, and radio-opaque markers of surgical materials that have undergone affine transformations, which preserve certain relationships between physical points, for example, parallelism between the edge lines is maintained. This forms the basis for the approach taken in the existing embodiments of the invention that relays in normalized cross-correlation.

There are two phases in this approach: (1) the preprocessing phase, in which the models for the objects to be detected/identified are built, and (2) the recognition phase applied to novel images.

The preprocessing phase only needs to take place once for every type of object to be recognized by the software (an IMD or an RSFO). The goal of this phase is to construct representation of the object that can be used by the recognition algorithm. This may include collection of a tightly cropped view of the object from a variety of viewpoints covering a range of out-of-plane rotations; in-plane rotations (around z-axis) can be automatically and accurately generated by image warping. Multiple views of the object may be obtained by collecting a set of radiological images with the object in the scene, positioned in the desired range of poses; by rendering a set of synthetic views from a 3D model such as that generated by software like AutoCAD® (AutoCAD is a registered trademark of Autodesk, Inc., San Rafael, Calif.), or by other means. For most devices between 10 and 60 views are sufficient.

For appearance based methods, the desired representation is obtained by storing the multiple views as templates, after applying transformations that make subsequent recognition robust, such as contrast normalization, Gaussian smoothing, and cleanup by morphological image operation (noise removal). For part based methods, an additional step may involve extraction of parts represented in the same way; for methods that combine template- and part-based approaches, such as deformable part models, the parts may be learned automatically along with the optimal placement of template window on the object in each view, from a data set of radiological images in which known locations of the object are marked. The parts may be as large as the entire object, or as small as a few square pixel sized windows with characteristic points on the object.

The second phase involves applying the representation constructed in the first stage to the input image in which IMDs and/or RSFOs must be detected and identified. In template-based recognition, the detection may rely on normalized cross-correlation between the stored object templates and the image, on response of a linear filter constructed from a training set of known locations of the object in radiological images by means of a statistical learning algorithm such as the structured support vector machine, or another mechanism that computes score of a hypothetical match between every location in the image and the stored templates. In part based methods, in addition to the mechanism described above, this may include similar computation for every part. The part scores may be combined in a shape-aware model, or, as in one existing embodiment of the invention, by means of anisotropic kernel diffusion, to contribute to the score of the regions(s) highly likely to contain the object. Finally, performing non-maxima suppression to eliminate redundant detections, and suppressing detections with match score below threshold (tuned by an automatic method with the objective to obtain the desired specificity/sensitivity), yields a (possibly empty) set of hypothesized detections.

Upon producing non-empty set of detection hypotheses, detection of the RSFO is automatically provided since it is linked to the templates generated in the first phase. Further verification phase is possible, by means of applying a statistical classification method trained on examples of radiographic images with known identity of objects (IMD or RSFO). Examples of classification techniques applicable here include logistic regression, support vector machines, boosting, and decision trees.

Again, 2D contours of RSFOs on radiographic images are analyzed as axonometric projections of 3D models of the surgical instruments, needles, and radio-opaque markers of surgical materials that have undergone affine transformations, which preserve certain relationships between physical points. Because, for example, parallelism between the edge lines is maintained, the correspondences between 2D image features and the known 3D model features (known as the model base) are not independent. These invariants governed by geometric constraints also form the basis for geometric hashing. Thus, another approach is based on geometric hashing algorithms (but not necessary limited to these).

There are two distinct phases in geometric hashing algorithms: (1) the preprocessing phase, involving finding specific unique feature points in the model; and (2) analysis and recognition phase. The preprocessing phase needs to take place only once (off-line), and may be conducted independently of real-time image analysis and the recognition phase (on-line). In the preprocessing phase, a series of steps are conducted for each object recognized. Briefly: a) A 3D model (such as generated by software like AutoCAD® (AutoCAD is a registered trademark of Autodesk, Inc., San Rafael, Calif.)) of surgical instrument, needle, or radio-opaque marker, obtained either from the manufacturer or generated by 3D scanner, is converted into stereo-lithography—triangular representation of a 3D surface geometry ("STL") format which defines the geometry of an object; b) Using 360 degree cuts, two-dimensional projection scenes of the device from multiple angles and perspectives are generated; c) Using edge and corner detection algorithms, unique feature points of the device are identified on each of these planar projection images. These are the model's feature points; d) For each ordered non-collinear triplet of feature points, affine coordinates of the remaining feature points are calculated using the original triplet as a basis; e) Each of these coordinates is entered into a hash table describing the relevant basis triplet, corresponding locations of feature points and a code identifying the device in question; and f) By repeating this algorithm for each feature point basis identified on each planar projection image derived from a 3D CAD model of each device, the pattern recognition software generates an STL database which may be used to recognize RSFOs in radiographic images.

In the second, recognition phase, radiographic image is analyzed in real-time to identify an RSFO in the X-ray images. The following steps are conducted in this embodiment: a) An input X-ray image is imported from the PACS or directly from portable X-ray machine software into the pattern recognition software, for example by using the API; b) The image is processed to remove/adjust imaging artifacts and adjust the contrast using appropriate algorithms; c) Using edge and corner detection algorithms (similar to those in the preprocessing phase), unique feature points are identified in the input image; d) An ordered, non-colinear triplet of interest feature points are arbitrarily selected in the input image. This is the arbitrary basis; e) Affine coordinates of the remaining feature points identified in the input image are calculated; f) For each such coordinate, the entire hash table contained in the external STL database is searched for a match; and g) If a sufficiently close match is identified in the hash table, a vote will be recorded for that entry.

This series of on-line real time steps is repeated for each arbitrary basis triplet identified on the input image. If sufficiently high number of votes are recorded for entries in the hash table that belong to the same surgical instrument, needle, or radio-opaque marker, it will be considered to be present in the analyzed image, and user notified—RSFO detected. Although geometric hashing algorithms are used in this exemplary embodiment of the invention, alternatively different algorithms (mentioned above) may be used to further optimize interface with STL data base.

One alternative approach is to use pattern recognition and rejection algorithms. This approach starts with methods of algorithm selection based on image preprocessing and pattern recognition using geometric algorithms including line detection, extraction of curve lines, semantic retrieval by spatial relationships, and structural object resulting in recognition algorithm using shape-form shading. Combination of point, line, peak and curve results in object recognition which is a commonly used technique in the computer vision applications. To implement an efficient pattern recognition technique or algorithm, the opposite pattern rejection algorithm must also be designed most specially for applications whenever numerous pattern recognitions are performed. Such pattern rejection must be able to define specific criteria about which pattern must be discriminated from among large classes of patterns. Therefore, rather than creating the axonometric projections database of 3D models of all standard small surgical instruments, needles, and radio-opaque markers of surgical material, multiple X-ray images of the object may be used to create pattern recognition algorithm that analyzes geometric and structural patterns from a given image and produce pattern recognition and rejection algorithms that produce the best result when looking for a specific pattern. Pattern recognition algorithms have not been extensively used in the analysis of the radiological images. The utility of the pattern recognition algorithms/technology to the specific setting/problem of RSFO is tremendous. Such pattern recognition software provides more accurate (sensitivity and specificity >95) and faster/instantaneous identification of RSFOs in X-ray images then current radiographs protocols (sensitivity and specificity <60) that take 30-40 minutes for completion.

One embodiment was developed in MATLAB (MathWorks™, Natick, Mass., USA) and capable of identifying Accu-Sorb X-Ray Detectable USP Type VII Gauze (Medline Industries Inc., Beijing, China) radiopaque marker and 2-0 SS-695 Wax coated 3 Metric ⅜, 24 mm cutting needle (Syneture-Covidien, Mansfield, Mass., USA) from X-ray images in any given projection (3D/objects rotated around all there axes). The executable file and code are available in the attachment.

Again, the embodiments are contemplated that are primarily based on geometric hashing and similarly robust algorithms but this disclosure is not necessary limited to these. In some embodiments, recognition is based on normalized cross-correlation methods/algorithms.

Examples RSFOs:

The following examples show how embodiments of the system and methods of the invention could be used in clinical situations for identifying RSFOs. These examples include hypothetical elements showing how the system could be used.

First, consider a situation where there is a needle count discrepancy in the OR. After completion of the exploratory laparotomy operating room scrub nurse brings to the attention of the attending surgeon that the needle counts do not match. One of the needles used for wound closing is missing. While the rest of the OR ancillary staff are visually inspecting the floor and drapes to possibly identify the missing needle, the surgeon calls the radiologic technician for the X ray of the surgical field to determine whether the needle is left in the surgical wound. Patient remains under the general anesthesia. After the completion of the X-ray of the OR field, the attending surgeon and resident are not able to positively identify a needle in the X-ray image due to the multiple metal surgical staples and poorly adjusted contrast. The surgeon then requests the radiologic technician to use a touch screen LCD display on the portable X-ray machine to activate a RSFO recognition tool from the tool drop down menu. After activation of the RSFO identification function, the computer/software analyzes the image and instantaneously indicates the position of the needle in the X-ray image by encircling the small area and putting the tip of the arrow on the suspicious object in the image. Subsequently, the surgeon re-opens the wound, extracts the needle, and closes the wound again. Since the needle was left intra abdominally and close to the site of the intestinal anastomosis, it had potential to cause small bowel perforation and disintegration of anastomosis, both of which may be fatal, if this situation was not recognized.

Second, consider an example following conclusion of the kidney transplantation, just before the closure the operating room scrub nurse brings to the attention of the attending surgeon that the needle counts do not match. One of the needles is missing. While the rest of the OR ancillary staff are visually inspecting the floor and drapes to possibly identify the missing needle, the surgeon calls the radiologic technician for the X ray of the surgical field to determine whether the needle is left in the surgical wound. Patient remains under the anesthesia. After the completion of the X-ray of the OR field, the attending surgeon and resident are not able to positively identify the needle in the X-ray image due to the multiple metal surgical staples and poorly adjusted contrast. The surgeon then requests the radiologic technician to use a touch screen LCD display on the portable X-ray machine to activate RSFO recognition tool from the tool drop down menu. After activation of the RSFO identification function the computer/software analyzes the image and instantaneously indicates the position of the needle in the X-ray image by encircling the small area and putting the tip of the arrow on the suspicious object in the image. The indicated position is outside of the surgical incision area at the very periphery of the X-ray image. Subsequently, the surgeon finds the needle in the drape folding which was pierced by the needle. This prompts the additional draping to avoid contamination of the surgical field. The surgical wound is then closed in a safe manner without danger of the operation field contamination and the surgery is concluded uneventfully.

Consider a third example of neurological surgery where the operating room scrub nurse brings to the attention of the attending neurosurgeon that the sponge count does not match just before the final closure of the scalp skin. A sponge is missing. While the rest of the OR ancillary staff are recounting the sponges and visually inspecting the floor and drapes to possibly identify the missing sponge, the attending neurosurgeon calls the radiologic technician for the X ray of the surgical field to determine whether the sponge is left in the surgical wound. Patient remains under the general anesthesia. After the completion of the X-ray of the OR field, the attending neurosurgeon and resident analyzes the X-ray image. They are suspicious but not sure that sponge appears in the X-ray image due to the over-positioning of the multiple metal surgical staples and clips in the image, poorly adjusted contrast, and the fact that radio opaque sponge marker is folded multiple times and not showing in a characteristic manner. Subsequently, the surgeon requests the radiologic technician to use a RSFO recognition tool from the tool drop down menu on the portable C-arm X-ray machine software environment rather than consulting and calling radiology attending. In addition, it usually takes 10-20 minutes to upload images to PACS system from the portable X-ray machines. After activation of the RSFO identification function the computer/software analyzes the image and instantaneously indicates the position of the sponge in the X-ray image by encircling the area and putting the tip of the arrow on the suspicious radio opaque shadow in the image. This confirms the surgeon's suspicion and he subsequently orders several consecutive X-rays from different angles of C-arm rotation by the same machine with software used to determine the relative position of the sponge in the wound. The software clearly indicates the 3D position of the sponge just below the skull muscle facia over skull bone. This information enables the surgeon to extract the sponge with minimal side incision rather than exploring the entire wound which in this particular surgery location would have put the patient to significant risk of developing CSF leak or dural adhesions. Most importantly, if the sponge was unnoticed, the possibility of inflammatory reaction to foreign body/sponge or infection has a potential for a fatal outcome in this particular location.

Fourth, consider an example in which a piece of intestinal anastomosis tool fails to dislodge from the inserted sutures and got unintentionally left in the abdomen. A patient undergoes a bariatric surgery during which a surgeon performs several different intestinal anastomosis. He uses a stapling instrument that inserts multiple stitches and subsequently retracts from the anastomosis site. There is no discrepancy in sponge or needle counts. Surgery is uneventful, but on the routine post-operative day one abdomen X-ray image the radiology resident was automatically warned that there is a RSFO in the image/patient by the software. A piece of the stapling instrument that inserts multiple stitches and subsequently retracts from the anastomosis site is still near the anastomosis site. This piece is made of plastic which is radiolucent but still has a small metal part (difficult to identify for the radiologist due to multiple metal staples used in the surgery and still in place) which is identified by the software. In this setting the software is optimized under PACS environment to check all the routine postoperative images including X-rays and CT scans. Subsequently the attending surgeon is notified and the patient is taken back to the OR same day where the missing piece is removed from the anastomosis site. Since this particular piece is left intra abdominally and at the site of the intestinal anastomosis it definitely has potential to cause small bowel anastomosis necrosis/failure which could be potentially fatal in morbidly obese patients undergoing bariatric surgeries.

Consider a fifth example involving a patient with a sponge left in the shoulder during the surgery 1 year ago. In this example, a patient recently has a surgery at the outside hospital and presents to the anesthesia pain clinic with a chronic pain in the shoulder. Attending anesthesiologist orders standard X-rays of the shoulder to rule out arthritic changes of the joint as the main cause of pain and subsequently notices irregular radio opaque shadows on the image. He is not sure whether these are surgical stitches/wires, calcifications, or something else. He warns and consults with a radiology resident for a final read of the X-rays. He then uses the software from the drop down tool menu under the PACS environment to analyze the image. Software indicates that X-ray image/patient has a retained sponge in the shoulder and identifies the area of the image with the sponge by circle and by putting an arrow on the tip of the folded radio opaque sponge mark. From subsequent analysis of the antero-posterior and lateral images software determines that apposition of the sponge was beneath the upper edge of the scapula. Therefore, instead of potentially getting pain treatment by anesthesiology pain physician, the patient is referred to orthopedic surgeon who subsequently schedules surgery for the wound exploration and extracts the sponge.

In a sixth example, consider a situation involving a cranial closure bone plates number discrepancy in which a plate is left in the surgery site/wound. As explained below, the software identifies the plate, its position, and indicates that part of the plate is a missing/structural integrity problem. More precisely, during the closure of skull defect with the bone flap, the operating room scrub nurse brought to the attention of the neurosurgeon that one of the metal plates used for closing of the skull opening is missing—number of the plates on the bone flap did not match the number of plates handed in to surgeons/number of empty spots on the surgical tray set. While the OR ancillary staff are visually inspecting the floor and drapes to possibly identify the missing plate, the neurosurgeon calls a radiologic technician for the X ray of the surgical field to determine whether the plate was dropped in the surgery field or beneath the bone flap. Patient remains under the general anesthesia in stable condition. Before the X-ray of the surgical field is taken, the technician takes the bone flap with already attached plates and places it on scrub nurse instrumental stand. After the completion of the several different angle X-rays of the OR field, the attending neurosurgeon and resident are not able to positively identify the missing plate due to the multiple metal surgical staples, overlapping bone, and non-adequate image contrast. Neurosurgeon then requests the radiologic technician to use/activate a RSFO recognition tool from the tool drop down menu and specifically focus the search on neurosurgical instruments to maximize the speed of the analysis. After activation of the RSFO identification function, the computer/software analyzes the image and instantaneously indicates the position of the plate in the X-ray image by encircling the small area and putting the tip of the arrow on the suspicious object in the image. Projection of the plate is almost perpendicular to the X-ray axis and difficult to identify for the physicians on the projections they initially saw/analyzed. In addition, software indicates a structural integrity problem/that a part of the plate is missing. Neurosurgeon re-opens the wound, extracts the plate, and additionally explores the wound again for the small missing piece of plate. He finds the missing piece of the plate being caught in the dural suture and removes it. The surgery is then completed uneventfully. It is important to notice that if these pieces were not removed, they could have potentially caused tears of the dura and leak of the cerebrospinal fluid or even more serious consequences if the patient needed to have MRI imaging (common in these cases). More precisely, free metal pieces in the strong magnetic field could have potential to damage surrounding tissue. This is also relevant for the abdominal surgeries when the needle or its fragment is left intra-abdominally—which in the case of subsequent MRI imaging can cause serious injuries.

Consider a seventh example involving a needle count discrepancy in the OR during the emergent surgery in which a needle is left in the surgery site/wound and the software instantaneously identifies the needle and its position in the clinically unstable patient. Just before starting closure of muscular and skin layers of the emergent exploratory laparotomy trauma patient surgeon calls radiologic technician for the X ray of the surgical field in order to determine whether any of the needles, surgical instruments, or sponges were left in the surgical wound. This is a routine procedure in trauma surgeries where multiple teams work together—in this case abdominal, trauma, and vascular surgery teams. The patient remains under the anesthesia and is hemodynamically unstable. Knowing that he has an option of using RSFO software tool, the head surgeon decides to check for RSFOs instantaneously using the software following the completion of the X-rays rather then waiting approximately 30-40 minutes for the images to be uploaded to PACS and be read by attending radiologist. After the images taken and RSFO identification function uses the computer/software to analyze the images and instantaneously indicate the position of the needle in the X-ray image by encircling the small area and putting the tip of the arrow on the suspicious object in the image. Subsequently, the surgeon re-opens the deeper layer of the wound, extracts the needle, and closes it again. Subsequently the surgery is completed uneventfully, and patient transferred to the post-operative care unit. In this particular example, the surgeon was willing to risk 5-10 minutes to use portable X-ray machine, take the X-rays, and analyze them with the available software instantaneously. If this software was not available, it would typically take about 30-40 minutes to determine the same information by consulting radiology service with much lower accuracy rate. Considering the fact that the patient was not hemodynamically stable and needed urgent transfer to intensive care unit, the speed of the proposed software solution would be crucial. This is also relevant for non-emergent cases where this software could save significant operating room and anesthesia time.

In an eighth example, a surgical instrument is left in the surgery site/wound and the software identifies the surgical instrument. Just before starting closure of muscular and skin layers of the emergent exploratory laparotomy trauma patient surgeon calls radiologic technician for the X ray of the surgical field in order to determine whether any of the needles, surgical instruments, or sponges are left in the surgical wound. This is a routine procedure in trauma surgeries where multiple teams work together—in this case abdominal, trauma, and vascular surgery teams. The patient remains under anesthesia. After the images have been taken and RSFO identification function used, the computer/software analyzes the images and instantaneously indicates the position of the micro surgical retractor in the X-ray image by encircling the small area and putting the tip of the arrow on the suspicious object in the image. Subsequently, the surgeon re-opens the wound, extracts the instrument, and closes it again. The surgery is completed uneventfully, and patient is transferred to the post-operative care unit. Since the retractor was left intra-abdominally in this example and close to the site of the arterial anastomosis, it had potential to cause thrombosis or disintegration of anastomosis which could be fatal if this situation was not recognized.

The feasibility of one embodiment (limited to IMDs) has been partially evaluated in the study: Pattern Recognition Software Assisted Analysis of Diagnostic Images for Identification of Implanted Medical Devices (IMDs): Technology Feasibility Study by Gluncic V, Moric M, Shakhnarovich G, Toleikis, Kobsa S, Ansari S A, Tuman K. It was presented at the 2012 American Society of Anesthesiology Annual Meeting in Washington, D.C. and is hereby incorporated by reference.

While this disclosure has been described as having an exemplary design, the present disclosure may be further modified within the spirit and scope of this disclosure. This application is therefore intended to cover any variations, uses, or adaptations of the invention using its general principles. Further, this application is intended to cover such departures from the present disclosure as come within known or customary practice in the art to which this disclosure pertains.

What is claimed is:

1. A computer system comprising:
   a memory;
   a data source including one or more electronic medical images representative of a portion of a physical body and object data representative of a plurality of pre-determined objects, each of said objects including a plurality of projections relating to a plurality of implantable medical devices;
   a processor electrically coupled with the memory;
   wherein the memory has a machine-executable code stored thereon that causes the processor to:
   acquire at least one medical image from the data source depicting an unidentified object;
   analyze the medical image by comparing the medical image with at least a portion of the object data; and
   identify one or more characteristics of the unidentified object in the medical image responsive to the analysis.

2. The computer system of claim 1 wherein each of said projections includes an axonometric projection.

3. The computer system of claim 2 wherein each of said axonometric projections includes an affine transformation.

4. The computer system of claim 1 wherein each of said objects includes a template based on a corresponding plurality of axonometric projections.

5. A computer system comprising:
   a memory;
   a data source including one or more electronic medical images representative of a portion of a physical body and object data representative of a plurality of pre-determined objects, said object data representative of a plurality of pre-determined objects having been automatically processed to identify and extract relevant features;
   a processor electrically coupled with the memory;
   wherein the memory has a machine-executable code stored thereon that causes the processor to:
   acquire at least one medical image from the data source depicting an unidentified object;
   automatically analyze the medical image by comparing the medical image with at least a portion of the object data; and
   automatically identify one or more characteristics of the unidentified object in the medical image responsive to the analysis without input from a human operator wherein at least one characteristic identified involves the specific type of implantable medical device.

6. The computer system as recited in claim 5, wherein the object data is representative of a plurality of pre-determined implantable medical devices.

7. The computer system as recited in claim 6, wherein the object data includes an axonometric projection.

8. The computer system of claim 7 wherein each of said axonometric projections includes an affine transformation.

9. The computer system of claim 5 wherein at least one characteristic identified involves one of the disconnections of the leads, wire cracks, and casings cracks of the implantable medical device.

* * * * *